US011278221B2

(12) United States Patent
Hatch

(10) Patent No.: US 11,278,221 B2
(45) Date of Patent: Mar. 22, 2022

(54) OPTICAL PHYSIOLOGIC SENSOR DEVICES

(71) Applicant: REVEAL BIOSENSORS, INC., San Jose, CA (US)

(72) Inventor: Guy Meredith Hatch, Logan, UT (US)

(73) Assignee: REVEAL BIOSENSORS, INC., San Jose, CA (US)

( * ) Notice: Subject to any disclaimer, the term of this patent is extended or adjusted under 35 U.S.C. 154(b) by 11 days.

(21) Appl. No.: 16/826,744

(22) Filed: Mar. 23, 2020

(65) Prior Publication Data

US 2020/0237274 A1     Jul. 30, 2020

Related U.S. Application Data

(63) Continuation of application No. 15/332,230, filed on Oct. 24, 2016, now Pat. No. 10,638,960.

(Continued)

(51) Int. Cl.
*A61B 5/1455*     (2006.01)
*A61B 5/00*       (2006.01)

(52) U.S. Cl.
CPC ........ *A61B 5/14552* (2013.01); *A61B 5/0004* (2013.01); *A61B 5/0075* (2013.01);
(Continued)

(58) Field of Classification Search
CPC .............. A61B 5/1455; A61B 5/14551; A61B 5/14552; A61B 5/6823; A61B 5/6824;
(Continued)

(56) References Cited

U.S. PATENT DOCUMENTS 4,281,645 A    8/1981  Jobsis
4,380,240 A    4/1983  Jobsis et al.
(Continued)

FOREIGN PATENT DOCUMENTS

CN    108366737 A    8/2018
JP    S59189828 U    12/1984
(Continued)

OTHER PUBLICATIONS

"Facts About Retinopathy of Prematurity," National Eye Institute, https://nei.nih.gov/health/rop/rop.
(Continued)

*Primary Examiner* — Eric F Winakur
(74) *Attorney, Agent, or Firm* — Buchalter; Cecily Anne O'Regan

(57) ABSTRACT

Physiologic sensors and methods of application are described. These sensors function by detecting recently discovered variations in the spectral optical density at two or more wavelengths of light diffused through the skin. These variations in spectral optical density have been found to consistently and uniquely relate to changes in the availability of oxygen in the skin tissue, relative to the skin tissue's current need for oxygen, which we have termed Physiology Index (PI). Current use of blood gas analysis and pulse oximetry provides physiologic insight only to blood oxygen content and cannot detect the status of energy conversion metabolism at the tissue level. By contrast, the PI signal uniquely portrays when the skin tissue is receiving 'less than enough oxygen,' just the right amount of oxygen,' or 'more than enough oxygen' to enable aerobic energy conversion metabolism. The PI sensor detects one pattern of photonic response to insufficient skin tissue oxygen, or tissue hypoxia, (producing negative PI values) and a directly opposite photonic response to excess tissue oxygen, or tissue hyperoxia, (producing positive PI values), with a neutral zone in between (centered at PI zero). Additionally, unique patterns of PI signal response have been observed relative to the level of physical exertion, typically with a secondary positive-going response trend in the PI values that appears to correspond with increasing fatigue. The PI sensor illuminates the skin with alternating pulses of selected wavelengths of red and infrared LED light, then detects the respective amount (Continued)

of light that has diffused through the skin to an aperture located a lateral distance from the light source aperture. Additional structural features include means of internally excluding light from directly traveling from the light emitters to the photodetector within the sensor. This physiology sensor and methods of use offer continuous, previously unavailable information relating to tissue-level energy conversion metabolism. Several alternative embodiments are described, including those that would be useful in medical care, athletics, and personal health maintenance applications.

35 Claims, 15 Drawing Sheets

Related U.S. Application Data

(60) Provisional application No. 62/246,374, filed on Oct. 26, 2015.

(52) U.S. Cl.
CPC ........... *A61B 5/0022* (2013.01); *A61B 5/6823* (2013.01); *A61B 5/6824* (2013.01); *A61B 5/6833* (2013.01); *A61B 2562/185* (2013.01)

(58) Field of Classification Search
CPC .... A61B 5/0004; A61B 5/0022; A61B 5/6832
See application file for complete search history.

(56) References Cited

U.S. PATENT DOCUMENTS

| | | | |
|---|---|---|---|
| 4,449,535 A | 5/1984 | Renault | |
| 4,554,924 A | 11/1985 | Engel | |
| 4,960,126 A | 10/1990 | Conlon et al. | |
| 5,497,769 A | 3/1996 | Gratton et al. | |
| 5,830,137 A | 11/1998 | Scharf | |
| 5,879,294 A | 3/1999 | Anderson et al. | |
| 6,801,799 B2 | 10/2004 | Mendelson | |
| 6,907,279 B2 * | 6/2005 | Sato .................. | A61B 5/14553 600/310 |
| 6,985,762 B2 | 1/2006 | Brashears et al. | |
| 7,254,430 B2 * | 8/2007 | Cho .................. | A61B 5/14532 600/316 |
| 7,313,424 B2 * | 12/2007 | Mayevsky ......... | A61B 5/14546 600/310 |
| 7,691,067 B2 | 4/2010 | Westbrook et al. | |
| 7,738,935 B1 | 6/2010 | Turcott | |
| 7,738,953 B2 | 6/2010 | Zhu et al. | |
| 8,073,516 B2 | 12/2011 | Scharf et al. | |
| 8,133,176 B2 | 3/2012 | Porges et al. | |
| 8,346,327 B2 | 1/2013 | Campbell et al. | |
| 10,638,960 B2 | 5/2020 | Hatch | |
| 2002/0016536 A1 | 2/2002 | Benni | |
| 2004/0034294 A1 | 2/2004 | Kimball et al. | |
| 2006/0009685 A1 | 1/2006 | Finarov et al. | |
| 2008/0081966 A1 | 4/2008 | Debreczeny | |
| 2008/0208009 A1 | 8/2008 | Shklarski | |
| 2010/0030041 A1 | 2/2010 | Bruinsma et al. | |
| 2010/0105997 A1 | 4/2010 | Ecker et al. | |
| 2010/0324390 A1 | 12/2010 | McLaughlin et al. | |
| 2011/0054336 A1 | 3/2011 | Jornod | |
| 2011/0205535 A1 | 8/2011 | Soller et al. | |
| 2011/0218413 A1 | 9/2011 | Wang et al. | |
| 2012/0053432 A1 | 3/2012 | Huiku et al. | |
| 2013/0109938 A1 | 5/2013 | Kuhn | |
| 2013/0303921 A1 | 11/2013 | Chu et al. | |
| 2013/0317331 A1 | 11/2013 | Bechtel et al. | |
| 2014/0275888 A1 | 9/2014 | Wegerich et al. | |
| 2015/0011854 A1 | 1/2015 | Frix et al. | |
| 2015/0057511 A1 | 2/2015 | Basu | |
| 2015/0173631 A1 | 6/2015 | Richards et al. | |
| 2016/0321395 A1 | 11/2016 | Colby et al. | |
| 2017/0112422 A1 | 4/2017 | Hatch | |

FOREIGN PATENT DOCUMENTS

| | | |
|---|---|---|
| JP | H0889500 A | 4/1996 |
| JP | H10295676 A | 11/1998 |
| JP | 2006326153 A | 12/2006 |
| JP | 2007515241 A | 6/2007 |
| JP | 2015530225 A | 10/2015 |
| JP | 2018536516 A | 12/2018 |
| WO | 2005060825 A1 | 7/2005 |
| WO | 2010144665 A1 | 12/2010 |
| WO | 2014055994 A1 | 4/2014 |
| WO | 2015168235 A1 | 11/2015 |
| WO | 2017074915 A1 | 5/2017 |

OTHER PUBLICATIONS

Azizbeigi, K., et. al., "Antioxidant enzymes and oxidative stress adaptation to exercise training: Comparison of endurance, resistance, and concurrent training in untrained males." J. Exerc. Sci. Fit., 12:1-6 (2014).

Baik N, et. al., "Cerebral haemorrhage in preterm neonates: does cerebral regional oxygen saturation during the immediate transition matter?," Arch Dis Child Fetal Neonatal Ed 100(5):F422-7, PMID: 26066762 (Sep. 2015).

Balu M, et. al., "In vivo multiphoton NADH fluorescence reveals depth-dependent keratinocyte metabolism in human skin," Biophysical Journal 104(1):258-67, PMID: 23332078 (Jan. 8, 2013).

Bangsbo, J. et. al. "Training and Testing the Elite Athlete," J. Exerc. Sci. Fit. 4(1) (2006).

Benini, R., et. al., "Influence of sex on cytokines, heat shock protein and oxidative stress markers in response to an acute total body resistance exercise protocol." J. Exerc. Sci. Fit. 13: 1-7 (2015).

Celik H, et. al., "Serum prohepcidin levels in premature newborns with oxygen radical diseases," J. Matern. Fetal Neonatal Med. 28(18):2228-33, PMID: 25363011 (2015).

Coquart, J., et. al., "Effects of a training program at the crossover point on the cluster of metabolic abnormalities and cardiovascular risk factors." J. Exerc. Sci Fit., 12: 73-79 (2014).

Dawson, JA, et. al., "Defining the reference range for oxygen saturation for infants after birth," Pediatrics 125:e1340-e1347, PMID: 20439604(2010).

Dey, S., et. al., "Compartment-specific control of reactive oxygen species scavengng by antioxidant pathway anzymes," J. Biol. Chem. PMID: 27048652 (Apr. 5, 2016).

Dice, et. al., "Patent ductus arteriosus: an overview." J. Pediatr Pharmacol Ther. 12(3):138-46. PMID: 23055849 (Jul. 2007).

Duun, et al. "A Ring Shaped Photodiode Designed for Use in a Reflectance Pulse Oximetry Sensor in Wireless Health Monitoring Applications," IEEE Sensors Journal, vol. 10(2) (Feb. 2010).

Eluamai, A., et. al., "Effect of aerobic exercise on mitochondrial DNA and aging." J. Exerc. Sci. Fit. 11: 1-5, (2013).

Fontaine et al. "Reflectance-Based Pulse Oximeter for the Chest and Wrist" Worcester Polytechnic Institute (2013).

Haahr, "A Novel Photodiode for Reflectance Pulse Oximetry in Low-Power Applications," Proceedings of the 29th Annual International Conference of the IEEE EMBS (Aug. 2007).

Hafner, et. al., "Hyperoxia in intensive care, emergency, and perioperative medicine: Dr. Jekyll or Mr. Hyde? A 2015 update," Ann Intensive Care 5(1):42, PMID: 26585328 (Dec. 2015).

Harms, FA, et.al., "Cutaneous mitochondrial respirometry: noninvasive monitoring of mitochondrial function," J. Clin. Monit. Comput. 29:509-519, PMID: 25388510 (2015).

Horiuchi, M., et. al., "Comparisons of energy cost and economical walking speed at various gradients in healthy, active younger and older adults." J. Exerc. Sci. Fit. 13: 79-85, (2015).

Jianxiong, W. et. al., "Exercise training at the maximal fat oxidation intensity improved health-related physical fitness in overweight middle-aged women.", J. Exerc. Sci. Fit., 13:111-116, (2015).

(56) References Cited

OTHER PUBLICATIONS

Lakshminrusimha, S, et. al., "Oxygen targeting in preterm infants: a physiologic interpretation," J. Perinatol. 35 (1):8-15, PMID: 25357098 (Jan. 2015).

Lawler, JM., et. al., "Mitochondria in the middle: Exercise preconditioning protection of striated muscle." J. Physiol., PMID:27060608 (Apr. 6, 2016).

Maia, M., et. al., "Maximal repetition performance, rating of perceived exertion, and muscle fatigue during paired set training performed with different rest intervals." J. Exerc. Sci. Fit., 13:104-110, (2015).

Manja V, et. al., "Oxygen saturation target range for extremely preterm infants: a systematic review and meta-analysis," JAMA Pediatr. 169(4):332-40, PMID: 25664703 (Apr. 2015).

Marseglia L, et. al., "Oxidative stress-mediated damage in newborns with necrotizing enterocolitis: a possible role of melatonin," PMID:25738791 (Aug. 2015).

Miller, et. al., "Antenatal antioxidant treatment with melatonin to decrease newborn neurodevelopmental deficits and brain injury caused by fetal growth restriction," J. Pineal Res. 56(3): 283-94. PMID: 24456220 (Apr. 2014).

Ovadia-Blechman, Z, et. al., "Noninvasive monitoring of peripheral microcirculatory hemodynamics under varying degrees of hypoxia," Respir. Physiol. Neurobiol. 22(216):23-27, PMID:26006296 (May 2015).

Parfit et. al., "A hard/heavy intensity is too much: The physiological, affective, and motivational effects (immediately and 6 months post-training) of unsupervised perceptually regulated training." J. Exerc. Sci. Fit. 13: 123-130, (2015).

Perrone, S, et. al., "The role of oxidative stress on necrotizing enterocolitis in very low birth weight infants," Curr. Pediatr. Rev. 10(3):202-7, PMID:25088341 (2014).

Pujary, "Investigation of Photodetector Optimization in Reducing Power Consumption by a Noninvasive Pulse Oximeter Sensor," Worcester Polytechnic Institute (2004).

Rei, M, et. al., "Neurological damage arising from intrapartum hypoxia/acidosis," Best Pract Res. Clin. Obstet Gynaecol; Best Pract. Res. Clin. Obstet. Gynaecol. PMID:26148854 (Jun. 21, 2015).

Stanula, A., et. al., "Calculating lactate anaerobic thresholds in sports involving different endurance preparation." J. Exerc. Sci. Fit., 11:12-18, (2013).

Suffoletto, B, et. al., "Near-infrared spectroscopy in post-cardiac arrest patients undergoing therapeutic hypothermia," J. Resuscitation 83(8):986-90, PMID: 22521725 (Aug. 2012).

Tokuhisa, T, et. al., "Outcome of infants with hypoxic ischemic encephalopathy treated with brain hypothermia," J. Obstet Gynaecol. Res. 41(2):229-37, PMID:25346401 (Feb. 2015).

Torres-Cuevas, et. al., "Oxygen supplementation to stabilize preterm infants in the fetal to neonatal transition: no satisfactory answer," Front Pediatr. 4:29, PMID:2714850 (Apr. 2016).

Verhagen, E, et. al., "Cerebral oxygenation in preterm infants with germinal matrix-intraventricular hemorrhages," Stroke 41(12):2901-7, PMID:20966409 (Dec. 2010).

Yli, MB, et. al., "Pathophysiology of foetal oxygenation and cell damage during labour," Best Pract Res. Clin. Obstet Gynaecol; 30:9-21, PMID:26211833 (Jun. 21, 2015).

Zhong-Wie, Z, et. a., "Mitochondrion-permeable antioxidants to treat ROS-burst-mediated acute diseases," Oxid. Med. Cell. Longev. 2016:6859523, PMID:26649144 (2016).

* cited by examiner

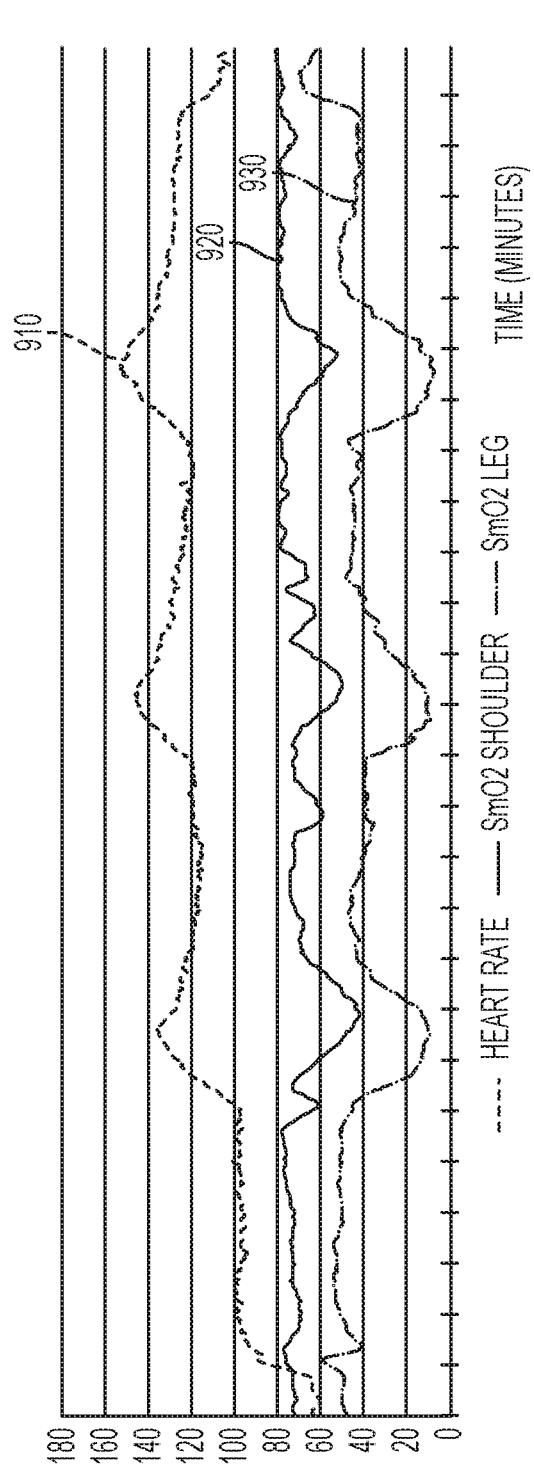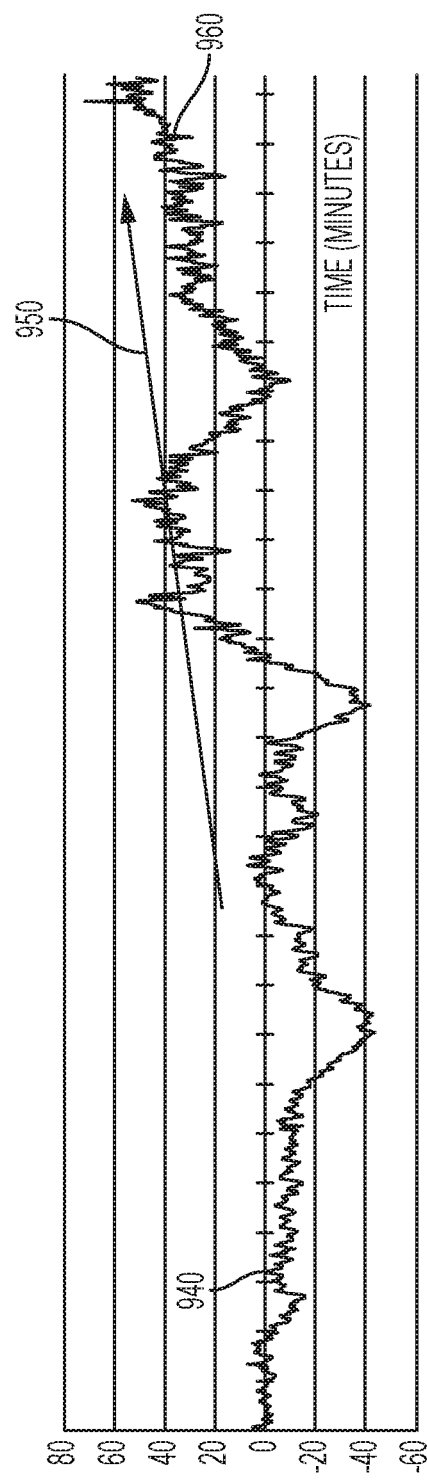
FIG. 9A
FIG. 9B

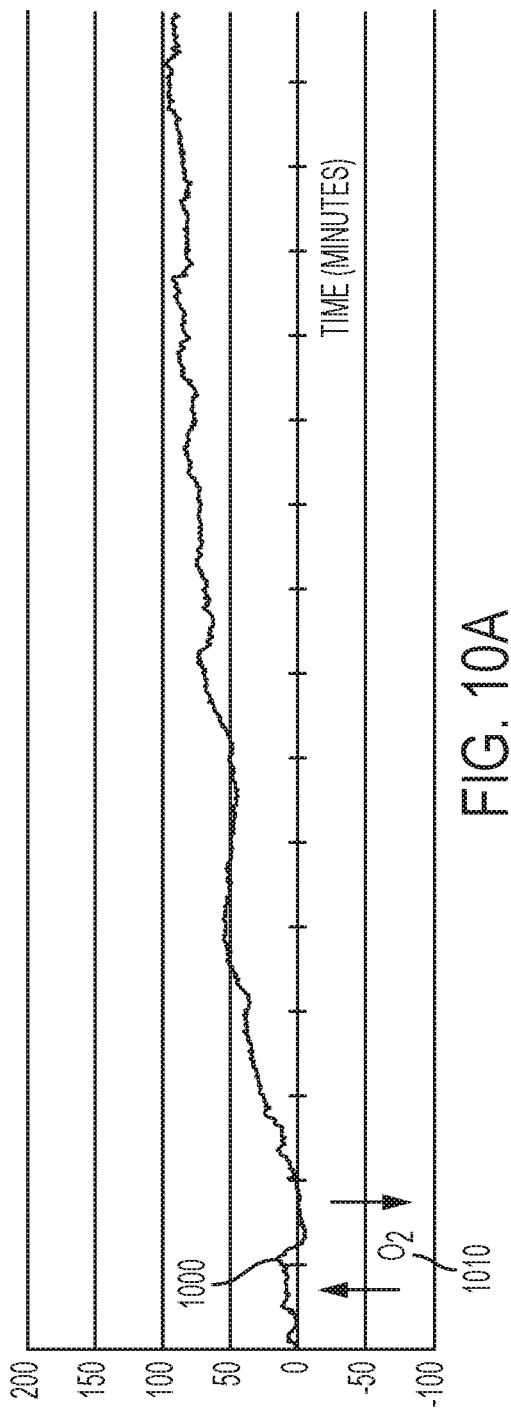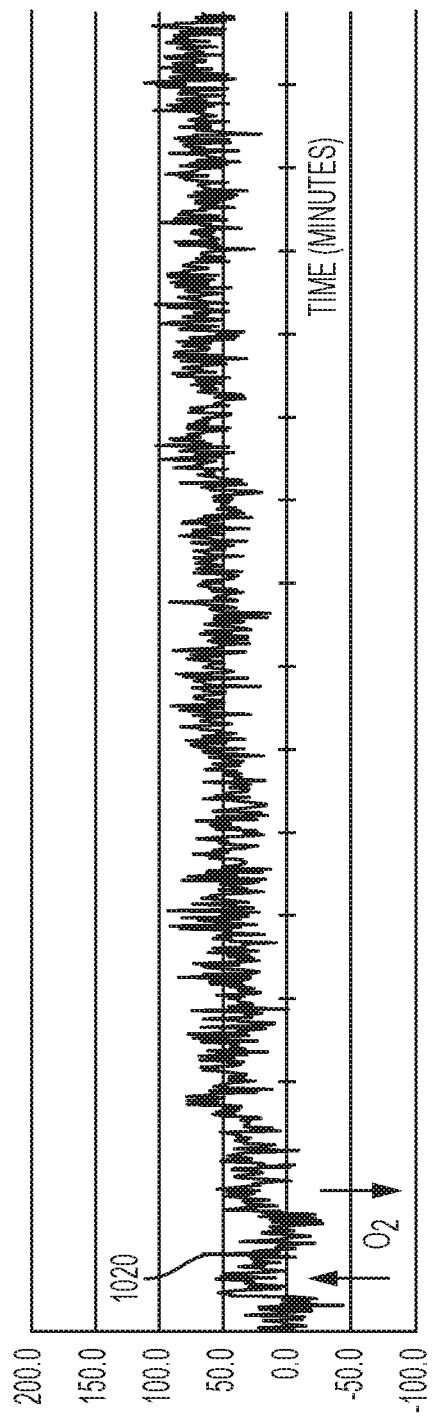

OPTICAL PHYSIOLOGIC SENSOR DEVICES

CROSS-REFERENCE

This application claims priority to U.S. patent application Ser. No. 15/332,230 filed Oct. 24, 2016 which claims the benefit of U.S. Provisional Application No. 62/246,374, filed Oct. 26, 2015, entitled OPTICAL PHYSIOLOGIC SENSORS AND METHODS which applications are incorporated herein by reference.

BACKGROUND

One of the primary life-dependencies of humans is continuous delivery of oxygen by the lungs and blood circulatory system to all tissues of the body in sufficient quantity to maintain aerobic metabolism; thus, avoiding tissue injury from too little, or too much oxygen. To approximate this information, clinicians must mentally correlate measurements of breathing gas oxygen fraction, breathing rate, heart rate, cardiac output, blood hemoglobin level, arterial blood hemoglobin-oxygen saturation ("blood gas," or $SaO_2$), and pulse oximetry ($SpO_2$), along with a subjective evaluation of arterial blood flow distribution. While each of these separate measurements are known to provide significant information, this currently available data, even with expert analysis, cannot provide the "bottom-line" tissue-level insight that has long been missing. Clinicians have long known that it is the tissue of vital organs, especially the brain, that is at risk of being injured; not the blood. The recently introduced Lumee™ sensor (Profusa), measures the oxygen level in tissue, but cannot indicate whether there is enough, or too much, oxygen. Also, the new sweat lactate sensor from Kenzen indicates when the skin is anaerobic, but cannot work when there is no sweat production and does not sense when too much oxygen is present. Without accurate, objective tissue-level information, the limitations of blood and tissue oxygen metrics, human sensory misperceptions, and subjective clinician assessment errors in this critical part of medical care can inadvertently result in permanent vital organ tissue damage and possibly death. Thus, there is an unmet need in critical care medicine for an objective, reliable, and preferably non-invasive indicator of oxygen-related energy conversion metabolism at the tissue level.

Personal need and desire for basic physiologic information is also found in many areas of normal living, such as maintenance of general health and conditioning, obesity weight loss exercise, maintaining safety in recreational and workplace activities, and athletic training and performance. While "medical device-like" vital sign monitoring devices have recently been re-packaged into consumer-friendly "activity tracker" devices, the same limitations remain with respect to their delivery of physiologic information.

SUMMARY

In one aspect of the disclosure, physiology index (PI) sensors with a suitable power source are configured to use about 660+/−10 nm and about 850+/−10 nm LED emitters. These two wavelength regions have been found, empirically, to produce the most pronounced divergence of the respective optical signal intensity from 850+/−10 nm light, relative to a simultaneously obtained signal intensity produced from 660+/−10 nm light. In the case of insufficient skin tissue oxygen supply, such as can be induced by briefly breathing nitrogen gas, the optical signal intensity from the 660+/−10 nm light, after it has diffused through skin tissue, has been found to diminish in intensity more rapidly than the signal from the 850+/−10 nm light after it has similarly diffused through skin tissue. Conversely, the presence of excessive tissue oxygen supply relative to skin tissue oxygen need and tolerance, such as can be induced by briefly breathing pure oxygen, has been found to produce a progressive, uniquely diverging optical signal from 850+/−10 nm light, relative to a simultaneously obtained signal produced from 660+/−10 nm light, with the optical signal intensity from the 850+/−10 nm light diminishing more rapidly than the signal from the 660+/−10 nm light, likely corresponding with progressively increased presence of products of reactive oxygen species (ROS) chemical reactions within the skin, such as with intake of increased oxygen fraction in the breathing gas, or at the end of an extended exercise activity. It should be noted that similar, but typically less pronounced, photonic responses have been found present within the spectral regions on either side of the above-listed center wavelengths of light, and that the above specification is exemplary only, and not intended to be exclusive, and is provided to be illustrative of the general concepts involved. It should also be noted that the disclosed PI signal is not a direct measurement of oxygen in the skin or in the blood. Rather, it is disclosed as an index of whether the current oxygen delivery rate to the skin tissue is less than, just right, or more than needed by the skin tissue for aerobic energy conversion at the skin tissue's current acclimation.

In another aspect of the disclosure, the two or more selected wavelengths of light may alternatively be obtained from a remotely located broadband incandescent lamp, with use of wavelength-specific band-pass filtering, or from remotely located LEDs or lasers, with transmission of the illumination light to the skin surface using optical fibers. Further, the light that has diffused through the subject's skin may be conveyed by optical fiber from the subject's skin surface to a remotely located detector. An alternative may be use of an unfiltered broadband light source for illumination, with the broadband light conveyed to the skin by optical fiber, and with return of the skin-diffused light by a separate optical fiber to a spectrometer for wavelength-specific detection and analysis. These alternative approaches, among others, may be effectively used for research purposes, or when the skin surface is immersed in water or otherwise cannot be accessed by electrical wiring.

Another aspect of the disclosure are the methods of calibration, data calculation, and display as these relate to the physiology being monitored. Most currently used biometrics are scalar, meaning that they are calibrated, calculated, and displayed as continuous numeric scales. The recently discovered PI signal, on the other hand, is observed to uniquely have a central numeric value region, with differing and discernable signal deviation patterns on either side. By convention, the middle of the central region is disclosed as "PI zero," with one discernable deviation pattern going progressively more negative, and the other deviation pattern going progressively more positive in numerical value. The calculated PI information is being disclosed as an index, and not as a means of identifying or measuring the presence or concentration of specific molecules within the skin. Therefore, the numeric rate of change of PI value was initially defined to provide acceptable numeric resolution using existing electronic components and software control and calculation methods. Also, it has been found through experimental observation that there is a need to accommodate the naturally wide variation in degree of skin pigmentation, the range of skin tissue opacity to the wavelengths used, and possibly other normal variations that must be accommodated to create a practical biometric instrument.

A normalization process is also disclosed whereby the initial PI zero value is established and the resolution of the PI value calculation is optimized. This process starts by step-wise ramping up, under software control, the power to the 660+/−10 nm (RED) LED, with the sensor secured on the desired surface of the skin of the user who is at rest, until the digital count of the sensor signal to the analog-to-digital (A/D) converter results in an output value at about the 80% of the maximum A/D count. The RED LED power level is then fixed in control memory. The power to the 850+/−10 nm (IR) LED is then step-wise ramped up until it's detected A/D count is just less than (i.e. one IR LED power level step less than) the A/D count produced by the RED LED at its fixed power level; whereupon the IR led power level is fixed in control memory. Alternating signal samples at each of these wavelengths are then obtained at 1 second intervals and the average difference in A/D count over one minute is calculated. This averaged offset value is then stored in control memory to be used as a fixed bias offset such that when the A/D count value of the IR sample is subtracted from the A/D count value of the RED sample, less the fixed bias offset, the beginning PI value is zero. Subsequent measurements and calculations continue to use the fixed bias in calculating the PI value as the user, for example, performs an exercise routine.

The disclosed physiologic sensors are configurable to detect, by two-, or multi-wavelength photonic signal variation, an accumulation of molecular reaction intermediates of anaerobic (i.e. glycolysis) energy conversion metabolism in skin or other body tissue. The detected signal from a sensor placed on the skin or surgically exposed internal organ can also be used as an indicator of excessive tissue oxygen delivery rate for aerobic (i.e. glycolysis+Krebs Cycle) energy conversion metabolism; as a surrogate, or direct index, respectively, of the adequacy of the tissue oxygen delivery rate needed to meet, but not exceed the safe limits of, the vital internal organ tissue's need for oxygen to perform energy conversion with minimal injury.

Another aspect of the disclosure is directed to photonic physiologic sensors that are configured to detect, by two-, or multi-wavelength photonic signal variation, what is believed to be an accumulation of molecular reaction products in the skin resulting from excess highly reactive oxygen free radical atoms (e.g. $O^-$) or molecules (e.g. $O_2^-$ and $OH^-$, $H_2O_2$, NO, etc., also referred to as reactive oxygen species, or ROS) combining, by spontaneous chemical reaction, with tissue and cellular lipid, protein, and DNA molecules in the skin. In some cases, such as with premature infants, current published research is increasingly emphasizing the need to prevent the accumulation of excess ROS in the brain, eyes, and gut. The disclosed PI monitoring method is presented as a rapidly responsive, non-invasive surrogate index for detecting the accumulation of such ROS excess in vital organ tissues.

Disclosed are photonic sensors that are non-invasive and minimally affected by common sources of mechanical, electronic, electromagnetic, and optical signal noise. Moreover, the disclosed sensors are configurable to respond in a timely fashion to detect important physiologic changes within the tissue/s being monitored. The disclosed sensors may be used to provide a feedback control signal for automated regulation of oxygen fraction in the breathing gas to help prevent vital organ injury from either tissue hypoxia or hyperoxia during surgical anesthesia and critical medical care. Additionally, the disclosed sensors can be embodied in a variety of comfortable, wearable formats compatible with use on adults and children for a wide variety of outpatient medical and non-medical applications. Users of such various embodiments may include, for several needful examples, medical and surgical patients of all ages and sizes, and at all levels of pathology, and athletes and workers in high risk occupations. In at least some configurations and applications, sensors are configurable to also provide an adjunct reflectance pulse oximeter ($SpO_2$) sensor function, as, for example, for use with newborn infants suffering from lung disease, where it is also important to monitor arterial hemoglobin/oxygen saturation as an index of lung function. Such an infant-specific format could be created to be compatible with use in the newborn intensive care setting and integrated into the electrocardiogram (ECG) contacts placed on the infant's chest and abdomen.

The disclosed sensors are also configurable to prevent emitted light from directly shunting from the light emitter/s to the light detector within the sensor housing. In some configurations, an empirically-derived lateral offset distance is applied between the apertures for the light emitters and detector element. In a fiber optic configuration, the optical fibers may be brought to illuminate adjacent regions of the skin surface via separate sheaths and apertures. Applications to surgically-exposed internal organs may, likewise, use optical fibers, with the illumination and detection apertures located in various configurations. The optical fibers may also be temporarily implanted within solid organs for research, or surgical or medical care monitoring purposes, with their exposed ends arrayed in various configurations to optimize the photonic signals received.

Yet another aspect of the disclosure is directed to optical physiologic sensors that are configured to detect, by two-, or multi-wavelength photonic signal variation, an abnormal skin microcirculatory regulation and/or skin tissue metabolic response to systemically circulating bacterial endotoxin as an early indicator of the onset of pathologic sepsis-induced inflammatory dysregulation of blood perfusion distribution; as a surrogate index of impending circulatory compromise of more vital body tissues.

Another aspect of the disclosure is directed to diffusion optical physiologic sensors that are configured to detect, by two-, or multi-wavelength photonic signal variation, the skin microcirculatory and/or skin tissue metabolic response to insufficient systemic circulatory volume loading, such as due to, for example, general body dehydration, blood loss from trauma, or blood loss during surgical operation; as a surrogate index for perfusion of vital organ tissues, where normal life-preserving autonomic nervous system reflex responses attempt to sustain the perfusion of vital organs at the expense of perfusion of the skin.

Also disclosed are physiologic sensors that are configured be continuously wearable in order to detect gradual exacerbation of chronic, progressive ailments including, for example, heart failure and/or chronic obstructive pulmonary disease (COPD), such that impending crises can be detected early enough to enable cost-effective outpatient care, instead of gradually progressing unnoticed until hospital admission or re-admission becomes a crisis imperative.

A physiologic sensor and/or blood oximeter sensor is disclosed using a "blue enhanced" NIR PIN photodiode, or equivalent alternative, having an upward ramping spectral sensitivity between about 600 nm and about 950 nm. Additionally, such a sensor package can include a metal, or otherwise opaque to visible through near-infrared (NIR) wavelengths, light shield between the light emitters and the photodetector, to reduce light shunting within the sensor package. Additionally, such a sensor may be configured with a 5 mm to 9 mm lateral separation between emitter and detector optically clear compound-potted apertures. In some configurations, the sensor may be designed for application to certain skin surfaces, such as, but not limited to, the chest or arm of adults, or the chest, abdomen, or extremities of infant patients, and for application to internal organ surfaces or temporary implantation within solid organ tissues during and/or following surgical operation.

Additional aspects of the disclosure include physiologic sensors that are configurable to detect, by two-, or multi-wavelength photonic signal variation, the degree of physiologic loading due to physical exertion. Physical exertion can be roughly segmented into two categories: (1) anaerobic, which can provide rapid onset, high force body motions over short periods of time, such as weight lifting and sprinting, and (2) aerobic, which can support much longer duration, but relatively lower intensity continuous body motions, such as marathon running. Athletes training for, and performing in one or the other type of activity have been found to benefit from narrowly defined, performance-specific types of training and conditioning exercise sessions. Examples of this include anaerobic-type performance needing multiple brief, high force generation cycles, with full recovery between, which has been found to stimulate up-regulation of enzyme systems needed for generation of adenosine triphosphate (ATP) by glycolysis. On the other hand, long distance runners have been found to benefit most from prolonged, fully aerobic exercise sessions, avoiding even brief periods of anaerobic metabolism, to up-regulate their enzyme systems needed for converting fats for use in aerobic energy conversion. Until the discovery of the PI signal, there has not been a convenient, objective, wearable method of sensing when the athlete is using primarily anaerobic, vs. aerobic energy conversion chemistry during exercise.

Another embodiment may integrate both PI and reflectance $SpO_2$ sensor functions, where these two biometrics each provide highly relevant, related, and complementary information in many useful applications. In this integrated format, such as for use on the chest and abdomen of a premature infant, the $SpO_2$ monitor function primarily provides an indication of the adequacy of the lungs to obtain oxygen, and the computed PI value provides an index of skin tissue oxygenation, as a surrogate for oxygen delivery by the blood to the brain and other vital internal organs. Existing $SpO_2$ monitors are well known to be easily compromised by sensor motion-induced optical signal artifacts that temporarily prevent accurate computation of the $SpO_2$ value, which, in turn, may trigger false alarms and, alternatively, may result in failure to initiate an alarm during real alarm conditions. On the other hand, the PI sensor is more quickly responsive to changes in oxygen delivery at the skin tissue level, and is inherently immune to sensor motion-induced signal artifact due to the tandem pattern of the variations that occur in the raw signal values with sensor motion. Thus, the PI value can be safely and effectively relied upon to provide a backup index to eliminate false $SpO_2$ alarms and to avoid missing real $SpO_2$ alarm conditions accompanied by sensor motion.

The disclosed sensors are also configurable to apply optimal wavelengths of emitted light and to select an optimum spectral sensitivity response profile of the light detector. Additionally, the disclosed sensors are configurable to have computer control, computer data processing, computer data storage, and wired or wireless data communications in accordance with existing capabilities, and expected future advances, in these areas of technology.

The disclosed sensors are configurable to be automatically initialized to accommodate natural variations in skin pigmentation, thickness, and spectral optical density at the two or more wavelengths of illumination light.

The disclosed sensors are also configurable to provide feedback signals to guide breathing gas blending of oxygen fraction, typically starting therapy at an oxygen fraction below atmospheric by blending oxygen with nitrogen gas, to avoid initially providing excessive oxygen to vital organ tissues above the tissue's need and tolerance level. By this new means, premature infants and patients being resuscitated from hypoxemia and/or ischemia stress, may be protected from inadvertent injury from excess oxygen delivery to vital organ tissues. Further, when specific patterns of change in the PI signal indicate the need, the disclosed sensors can be used to automatically command incremental increases in the breathing gas oxygen fraction in response to the oxygen need and tolerance of the skin, as a surrogate of internal vital organs, in non-invasive applications. Finally, with surface application to internal organs exposed surgically, or with fiber optic light guides inserted directly into solid organs, the PI signal is disclosed as a previously unavailable means of direct, real-time indication of vital organ tissue need for, and tolerance of, delivered oxygen via blood perfusion.

An aspect of the disclosure is directed to physiologic index sensors. Suitable sensors comprise: a first means for emitting a first wavelength wherein the first means for emitting the first wavelength is configurable to emit a first target wavelength of from 650 nm to 670 nm; a second means for emitting a second wavelength wherein the second means for emitting the second wavelength is configurable to emit a second target wavelength of from 840 nm to 860 nm; a detection means optically isolated from the first means for emitting the first wavelength and the second means for emitting the second wavelength; and a processor means configured to receive an input from the detection means. In some configurations, the physiologic index sensor further comprises a data transmitter means. Additionally, the physiologic index sensors can be configurable to determine one or more of an index of oxygen delivery and aerobic energy conversion. A housing means can be provided having a first aperture and a second aperture. Additional apertures can be provided without departing from the scope of the disclosure. Additionally, one or more of the apertures can be filled with an optically clear material. A securer means can be provided which is configured to secure the physiologic index sensor to a user, such as at an arm or a chest. One or more electrically conductive skin contact adhesive means can be provided. In some configurations, at least one of the first means for emitting the first wavelength and the second means for emitting the second wavelength is connected to a physiologic index sensor housing via a cable. Additionally, at least one of the first means for emitting the first wavelength and the second means for emitting the second wavelength is an unfiltered broadband light source, using optical fiber cables for light conveyance to and from the skin, and the detection means is a spectrometer, with selected wavelength intensity values obtained by the spectrometer used to compute the physiologic index.

Another aspect of the disclosure is directed to physiologic index sensors. Sensors can comprise: a first emitter for emitting a first wavelength wherein the first emitter for emitting the first wavelength is configurable to emit a first target wavelength of from 650 nm to 670 nm; a second emitter for emitting a second wavelength wherein the second emitter for emitting the second wavelength is configurable to emit a second target wavelength of from 840 nm to 860 nm; a detector optically isolated from the first emitter and the second emitter; and a processor configured to receive an input from the detector. The physiologic index sensors can further comprise a data transmitter. Additionally, the physiologic index sensors can be configurable to determine one or more of an index of oxygen delivery and aerobic energy conversion. A housing can be provided having two or more apertures. One or more apertures can be filled with an optically clear material. A securer can be configured to secure the physiologic index sensor to a user such as at an arm or a chest. One or more electrically conductive skin contact adhesive pads can also be provided. Additionally, at least one of the first emitter for emitting the first wavelength and the second emitter for emitting the second wavelength is connected to a physiologic index sensor housing via a cable. In some configurations at least one of the first emitter for emitting the first wavelength and the second emitter for emitting the second wavelength is an unfiltered broadband light source, with two or more wavelength intensity values being selected by a spectrometer to be used to compute a physiologic index value.

Still another aspect of the disclosure is directed to physiologic index sensors comprising: a housing adapted to engage a chest or an arm of a user wherein the housing has a first aperture and a second aperture; a first emitter wherein the first emitter is configurable to emit a first wavelength of from 650 nm to 670 nm through the first aperture; a second emitter wherein the second emitter is configurable to emit a second wavelength is configurable to emit a second target wavelength of from 840 nm to 860 nm; a detector disposed within the housing wherein the detector is optically isolated in the housing from the first emitter and the second emitter and adjacent the second aperture; and a processor configured to receive an input from the detector. The physiologic index sensors can further comprise a data transmitter. Additionally, the physiologic index sensor is configurable to determine one or more of an index of oxygen delivery and aerobic energy conversion. Two or more apertures can be provided which can be filled with an optically clear material. A securer can be provided which is configured to secure the physiologic index sensor to a user, such as to the arm or the chest of the user. In some configurations, at least one of the first emitter for emitting the first wavelength and the second emitter for emitting the second wavelength is connected to a physiologic index sensor housing via a cable. Additionally, at least one of the first emitter for emitting the first wavelength and the second emitter for emitting the second wavelength is an unfiltered broadband light source, with two or more wavelength intensity values being selected by a spectrometer to be used to compute a physiologic index value.

Yet another aspect of the disclosure is directed to methods of detecting a biological parameter. Suitable methods comprise: placing a physiologic index sensor in contact with an arm or a chest of a patient wherein the physiologic index sensor further comprises, a first emitter for emitting a first wavelength wherein the first emitter for emitting the first wavelength is configurable to emit a first target wavelength of from 650 nm to 670 nm, a second emitter for emitting a second wavelength wherein the second emitter for emitting the second wavelength is configurable to emit a second target wavelength of from 840 nm to 860 nm, a detector optically isolated from the first emitter and the second emitter, and a processor configured to receive an input from the detector; powering the physiologic index sensor with a power supply; emitting a light in a first wavelength and emitting a light in a second wavelength; detecting a diffused light through a tissue; and analyzing the detected signal produced by the diffused light. Additional steps can include one or more of the step of: determining an index of oxygen delivery for the patient; transmitting data from the physiologic index sensor to a second device; and detecting an excess oxygen level at a tissue.

Another aspect of the disclosure is directed to a communication system, comprising: a physiologic index sensor in contact with an arm or a chest of a patient wherein the physiologic index sensor further comprises, a first emitter for emitting a first wavelength wherein the first emitter for emitting the first wavelength is configurable to emit a first target wavelength of from 650 nm to 670 nm, a second emitter for emitting a second wavelength wherein the second emitter for emitting the second wavelength is configurable to emit a second target wavelength of from 840 nm to 860 nm, a detector optically isolated from the first emitter and the second emitter, and a processor configured to receive an input from the detector; a power supply in communication with the physiologic index sensor to power the physiologic index sensor; a server computer system; a measurement module on the server computer system for permitting a transmission of a measurement from the physiologic index sensor over a network; and at least one of an API engine connected to at least one of the physiologic index sensor to create a message about the measurement and transmit the message over an API integrated network to a recipient having a predetermined recipient user name, an SMS engine connected to at least one of a system for detecting physiological parameters and the physiologic index sensor to create an SMS message about the measurement and transmit the SMS message over the network to a recipient device having a predetermined measurement recipient telephone number, or an email engine connected to at least one of the physiologic index sensor to create an email message about the measurement and transmit the email message over the network to a recipient email having a predetermined recipient email address. Additionally, a storing module can be provided on the server computer system for storing the measurement in a physiologic index sensor server database. In some configurations, the physiologic index sensor is connectable to the server computer system over at least one of a mobile phone network or an Internet network, and a browser on a measurement recipient electronic device is used to retrieve an interface on the server computer system. Additionally, an interface can be provided on the server computer system, the interface being retrievable by an application on a mobile device. The server computer system can be connectable over a cellular phone network to receive a response from a measurement recipient mobile device. A downloadable application can be provided which resides on a measurement recipient mobile device, the downloadable application transmitting a response and a measurement recipient phone number ID over a cellular phone network to the server computer system, the server computer system utilizing the measurement recipient phone number ID to associate the response with an SMS measurement.

Still another aspect of the disclosure is directed to a method of obtaining a physiologic index comprising: deploying a physiologic index sensor having a first emitter for emitting a first wavelength wherein the first emitter for emitting the first wavelength is configurable to emit a first target wavelength of from 650 nm to 670 nm, a second emitter for emitting a second wavelength wherein the second emitter for emitting the second wavelength is configurable to emit a second target wavelength of from 840 nm to 860 nm, a detector optically isolated from the first emitter and the second emitter, and a processor configured to receive an input from the detector, powering the physiologic index sensor with a power supply; adjusting a first target wavelength light source power level until a resulting signal intensity is about 80% of a sensor system A/D converter maximum count limit; recording and locking the first target wavelength light source power level in a control memory; adjusting a second target wavelength light source power level until a resulting signal intensity is less than the signal intensity produced by the first target wavelength light source; recording and locking the second target wavelength light source power level in the control memory; using the respective locked first and second target wavelength light source power levels to sample a spectral optical density at a sensor site once per second at the first and second target wavelengths; computing an average difference from the first target wavelength signal intensity minus the second target wavelength signal intensity; and recording and locking the average difference in the control memory. In some configurations, the method includes computing an average difference from the first target wavelength signal intensity minus the second target wavelength signal intensity is performed over 1 minute. Additionally, an initialization process can be used to accommodate one or more of a natural or abnormal variation in a skin pigmentation and a natural or abnormal variation in a spectral optical density of the skin tissue. In some methods the methods can include sampling each of the first and second target wavelength signals, minus a time-adjacent, un-illuminated background signal; and subtracting the second target wavelength signal intensity value plus the recorded bias offset value from the first target wavelength signal intensity value to produce a physiologic index value. Additionally, the sampling and subtracting steps can be repeated. Displaying and recording the physiologic index value can be performed in a one, or more second timed basis. The methods can further comprise: setting a starting oxygen fraction level at 15% oxygen; increasing the oxygen fraction by 1%; monitoring the physiologic index for 15 seconds for a change in oxygen fraction; if the second target wavelength signal intensity value does not decrease, and the first target wavelength signal intensity increases in response to the 1% increase in oxygen fraction generating a feedback control command to increase the breathing gas oxygen fraction by 1%. The method can further comprise repeating the monitoring and response command cycle by at least one of: if the second target wavelength signal intensity decreases, and the first target wavelength signal intensity does not increase in response to a 1% increase in oxygen fraction in the breathing gas, decrease the breathing gas fraction by 1% and monitor the physiologic index for one minute; if the first target wavelength signal intensity decreases in response to the 1% decrease in oxygen fraction in the breathing gas increase the breathing gas oxygen fraction by 1%; and if the second target wavelength signal intensity does not decrease, and the first target wavelength signal intensity does not increase in response to a 1% increase in the oxygen fraction of the breathing gas, the subject's physiologic index "zero" condition has been reached, resulting in a one-minute averaging of the offset of once-per-second samples of the first target wavelength signal intensity minus the second target wavelength signal intensity, resulting in recording and locking a new bias offset value in a control menu and indicating that a physiologic index "zero" has been reset.

INCORPORATION BY REFERENCE

All publications, patents, and patent applications mentioned in this specification are herein incorporated by reference to the same extent as if each individual publication, patent, or patent application was specifically and individually indicated to be incorporated by reference. References include, for example:
U.S. Pat. No. 5,830,137 A to Scharf issued Nov. 3, 1998 for "Green Light Pulse Oximeter;"
U.S. Pat. No. 6,801,799 B2 to Mendelson, issued Oct. 5, 2004, for "Pulse Oximeter and Method of Operation;"
U.S. Pat. No. 7,691,067 B2 to Westbrook, issued Apr. 6, 2010, for "Method for Measuring Central Venous Pressure or Respiratory Effort;"
U.S. Pat. No. 7,738,935 B1 to Turcott, issued Jun. 15, 2010, for "Methods and Devices for Reduction of Motion-Induced Noise in Pulse Oximetry;"
U.S. Pat. No. 8,073,516 B2 to Scharf issued Dec. 6, 2011, for "Separating Motion from Cardiac Signals Using Second Order Derivative of the Photo-Plethysmogram and Fast Fourier Transforms;"
U.S. Pat. No. 8,133,176 B2 to Porges, issued Mar. 13, 2012, for "Method and Circuit for Indicating Quality and Accuracy of Physiological Measurements;"
U.S. Pat. No. 8,346,327 B2 to Campbell, issued Jan. 1, 2013, for "Method for Identification of Sensor Site by Local Skin Spectrum Data;"
US 2006/0009685 A1 to Finarov et al. published Jan. 12, 2006 for "Device and Method for Non-Invasive Optical Measurements;"
US 2008/0208009 A1 to Shklarski published Aug. 29, 2008 for "Wearable Device, System and Method for Measuring Vital Parameters;"
US 2008/0081966 A1 to Debreczeny published Apr. 3, 2008 for "Symmetric LED Array for Pulse Oximetry;"
US 2010/0324390 A1 to McLaughlin, published Dec. 23, 2010, for "Measurement of Oxygen Saturation of Blood Haemoglobin,"
US 2011/0054336 A1 to Jornod published Mar. 3, 2011 for "Method and Device for Measuring the Pulse by Means of Light Waves with Two Wavelengths;
US 2013/0317331 A1 to Bechtel, published Nov. 28, 2013, for "Monte Carlo and Iterative Methods for Determination of Tissue Oxygen Saturation;"
US 2015/0057511 A1 to Basu, published Feb. 26, 2015, for "Sensor and Method for Continuous Health Monitoring;"
US 2015/0011854 A1 to Frix, published Jan. 8, 2015, for "Continuous Transdermal Monitoring System and Method;"
US 2013/0303921 A1 to Chu, published Nov. 14, 2013, for "System and Method for Measurement of Physiological Data with Light Modulation;"
US 2014/0275888 A1 to Wegerich published Sep. 18, 2014 for "Wearable Wireless Multisensor Health Monitor with Heat Photoplethysmograph;"
WO 2015/168235 A1 to Hatch published Nov. 5, 2015, for "Physiological Sensors, Systems, Kits and Methods Therefor;"
"Facts About Retinopathy of Prematurity," National Eye Institute, https://nei.nih.gov/health/rop/rop;
Azizbeigi, K., et. al., "Antioxidant enzymes and oxidative stress adaptation to exercise training: Comparison of endurance, resistance, and concurrent training in untrained males." J. Exerc. Sci. Fit., 12:1-6 (2014);

Balk N, et. al., "Cerebral haemorrhage in preterm neonates: does cerebral regional oxygen saturation during the immediate transition matter?," Arch Dis Child Fetal Neonatal Ed 100(5):F422-7, PMID: 26066762 (September 2015);

Balu M, et. al., "In vivo multiphoton NADH fluorescence reveals depth-dependent keratinocyte metabolism in human skin," Biophysical Journal 104(1):258-67, PMID: 23332078 (Jan. 8, 2013);

Bangsbo, J. et. al. "Training and Testing the Elite Athlete," J. Exerc. Sci. Fit. 4(1) (2006);

Benini, R., et. al., "Influence of sex on cytokiones, heat shock protein and oxidative stress markers in response to an acute total body resistance exercise protocol." J. Exerc. Sci. Fit. 13: 1-7 (2015);

Celik H, et. al., "Serum prohepcidin levels in premature newborns with oxygen radical diseases," J. Matern. Fetal Neonatal Med. 28(18):2228-33, PMID: 25363011 (2015);

Coquart, J., et. al., "Effects of a training program at the crossover point on the cluster of metabolic abnormalities and cardiovascular risk factors." J. Exerc. Sci. Fit., 12: 73-79 (2014);

Dawson J A, et. al., "Defining the reference range for oxygen saturation for infants after birth," Pediatrics 125:e1340-e1347, PMID: 20439604 (2010); Dey, S., et. al., "Compartment-specific control of reactive oxygen species scavengng by antioxidant pathway enzymes," J. Biol. Chem. PMID: 27048652 (Apr. 5, 2016);

Dice, et. al., "Patent ductus arteriosus: an overview." J. Pediatr Pharmacol Ther. 12(3):138-46. PMID: 23055849 (July 2007);

Duun, et al. "A Ring Shaped Photodiode Designed for Use in a Reflectance Pulse Oximetry Sensor in Wireless Health Monitoring Applications," IEEE Sensors Journal, Vol. 10(2) (February 2010);

Eluamai, A., et. al., "Effect of aerobic exercise on mitochondrial DNA and aging." J. Exerc. Sci. Fit. 11: 1-5, (2013);

Fontaine et al. "Reflectance-Based Pulse Oximeter for the Chest and Wrist" Worcester Polytechnic Institute (2013);

Gaynor, P., et. al., "A hard/heavy intensity is too much: The physiological, affective, and motivational effects (immediately and 6 months post-training) of unsupervised perceptually regulated training." J. Exerc. Sci. Fit. 13: 123-130, (2015);

Haahr, "A Novel Photodiode for Reflectance Pulse Oximetry in Low-Power Applications," Proceedings of the 29th Annual International Conference of the IEEE EMBS (August 2007);

Hafner, et. al., "Hyperoxia in intensive care, emergency, and peri-operative medicine: Dr. Jekyll or Mr. Hyde? A 2015 update," Ann Intensive Care 5(1):42, PMID: 26585328 (December 2015);

Harms, F A, et. al., "Cutaneous mitochondrial respirometry: non-invasive monitoring of mitochondrial function," J. Clin. Monit. Comput. 29:509-519, PMID: 25388510 (2015);

Horiuchi, M., et. al., "Comparisons of energy cost and economical walking speed at various gradients in healthy, active younger and older adults." J. Exerc. Sci. Fit. 13: 79-85, (2015);

Jianxiong, W. et. al., "Exercise training at the maximal fat oxidation intensity improved health-related physical fitness in overweight middle-aged women.", J. Exerc. Sci. Fit., 13:111-116, (2015);

Lakshminrusimha, S, et. al., "Oxygen targeting in preterm infants: a physiologic interpretation," J. Perinatol. 35(1): 8-15, PMID: 25357098 (January 2015);

Lawler, J M., et. al., "Mitochondria in the middle: Exercise preconditioning protection of striated muscle." J. Physiol., PMID: 27060608 (Apr. 6, 2016);

Maia, M., et. al., "Maximal repetition performance, rating of perceived exertion, and muscle fatigue during paired set training performed with different rest intervals." J. Exerc. Sci. Fit., 13:104-110, (2015);

Manja V, et. al., "Oxygen saturation target range for extremely preterm infants: a systematic review and meta-analysis," JAMA Pediatr. 169(4):332-40, PMID: 25664703 (April 2015); Marseglia L, et. al., "Oxidative stress-mediated damage in newborns with necrotizing enterocolitis: a possible role of melatonin," PMID: 25738791 (August 2015);

Miller, et. al., "Antenatal antioxidant treatment with melatonin to decrease newborn neurodevelopmental deficits and brain injury caused by fetal growth restriction," J. Pineal Res. 56(3): 283-94. PMID: 24456220 (April 2014);

Ovadia-Blechman Z, et. al., "Noninvasive monitoring of peripheral microcirculatory hemodynamics under varying degrees of hypoxia," Respir. Physiol. Neurobiol. 22(216): 23-27, PMID: 26006296 (May 2015);

Perrone S, et. al., "The role of oxidative stress on necrotizing enterocolitis in very low birth weight infants," Curr. Pediatr. Rev.10(3):202-7, PMID: 25088341 (2014);

Pujary, "Investigation of Photodetector Optimization in Reducing Power Consumption by a Noninvasive Pulse Oximeter Sensor," Worcester Polytechnic Institute (2004);

Rei M, et. al., "Neurological damage arising from intrapartum hypoxia/acidosis," Best Pract Res. Clin. Obstet Gynaecol; Best Pract. Res. Clin. Obstet. Gynaecol. PMID: 26148854 (Jun. 21, 2015);

Stanula, A., et. al., "Calculating lactate anaerobic thresholds in sports involving different endurance preparation." J. Exerc. Sci. Fit., 11: 12-18, (2013);

Suffoletto B, et. al., "Near-infrared spectroscopy in post-cardiac arrest patients undergoing therapeutic hypothermia," J. Resuscitation 83(8):986-90, PMID: 22521725 (August 2012);

Tokuhisa T, et. al., "Outcome of infants with hypoxic ischemic encephalopathy treated with brain hypothermia," J. Obstet. Gynaecol. Res. 41(2):229-37, PMID: 25346401 (February 2015);

Torres-Cuevas, et. al., "Oxygen supplementation to stabilize preterm infants in the fetal to neonatal transition: no satisfactory answer," Front Pediatr. 4:29, PMID: 2714850 (April 2016);

Verhagen E, et. al., "Cerebral oxygenation in preterm infants with germinal matrix-intraventricular hemorrhages," Stroke 41(12):2901-7, PMID: 20966409 (December 2010);

Yli M B, et. al., "Pathophysiology of foetal oxygenation and cell damage during labour," Best Pract Res. Clin. Obstet Gynaecol; 30:9-21, PMID: 26211833 (Jun. 21, 2015); and Zhong-Wie Z, et. a., "Mitochondrion-permeable antioxidants to treat ROS-burst-mediated acute diseases," Oxid. Med. Cell. Longev. 2016:6859523, PMID: 26649144 (2016).

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 9A-B are line graphs of data recorded, using a heart rate monitor, a Moxy Monitor ($SpO_2$ in a large muscle vs. fingertip), and a PI sensor using 660 nm and 850 nm light during an exercise challenge test;

FIGS. 10A-B are line graphs of data recorded, and of a derived PI using 660 nm and 850 nm LED light, in parallel with a QTH lamp light source and a spectrometer during a hyperoxia challenge test; breathing pure oxygen;

DETAILED DESCRIPTION

Figure 1A:
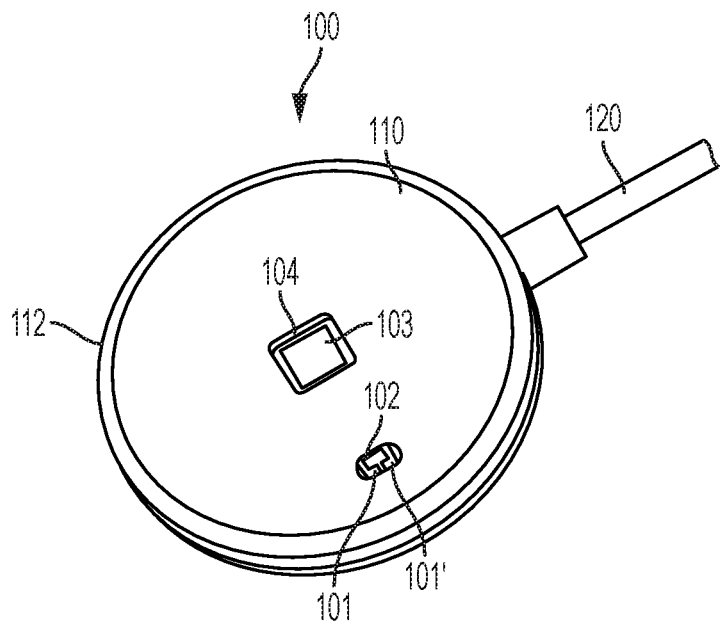
FIG. 1A illustrates the sensor viewed from the skin contact side.

The present disclosure provides an optically efficient tissue light diffusion/absorption mode sensor for monitoring spectral optical density variations that have been found to be associated with alterations in tissue metabolic chemistry. These sensors can be used on subjects of all ages and sizes to determine a Physiology Index (PI). As will be appreciated by those skilled in the art, the disclosed sensors are not blood oximeter devices, but rather, sensors configured to detect spectral photonic responses relating to, for example, mammalian skin tissue metabolic chemistry as two or more wavelengths of light pass through the tissue at the sensor site. Experimental data demonstrates that these sensor responses apparently result from accumulation of energy conversion metabolism-related molecules within the skin. Two distinct phases of response have been detected: (1) when the level of intracellular oxygen in skin tissue is not sufficient for aerobic energy conversion metabolism (negative PI values) and (2) when there is excess intracellular oxygen leading to potentially damaging, spontaneous chemical reactions between excess ROS and tissue component molecules (positive PI values). In between these two opposing signal response phases is a 'normal' tissue energy conversion metabolism status corresponding to fully acclimated aerobic tissue energy conversion metabolism (i.e. PI zero). Experimental challenge tests have shown strong circumstantial correlation between the imposed changes, e.g. by either increasing or decreasing the oxygen fraction of the breathing air, and the corresponding PI sensor signal responses revealing the status of skin tissue energy conversion metabolism.

As will be appreciated by those skilled in the art, both transmission (finger-tip) and reflectance (flat surface of the skin) $SpO_2$ sensors generate a continuous, scalar measurement of the percent hemoglobin-oxygen saturation, which is useful in assessing the gas exchange function in the lungs. However, neither transmission nor reflectance $SpO_2$ can reveal when the illuminated skin tissue is fully acclimated and experiencing normal aerobic metabolism in real time, or when the skin tissue is being provided too little or too much oxygen.

The disclosed sensor design is configurable for convenient placement on a subject's upper arm, held in place with an arm band, or on the chest, held in place with adhesive or a chest strap. These locations reduce the likelihood of sensor motion-generated artifact. A metallic light barrier can be provided within the sensor housing between the light emitter the photodetector to prevent shunting of the emitted light within the housing to the detector. The lateral separation between the light emitting diode (LED) light emitter aperture and the photodiode sensor aperture can be between 5 mm and 9 mm. In the preferred embodiment, two LEDs are provided, e.g. with center wavelengths at about 660 nm and about 850 nm, as the light emitters, and a "blue enhanced" silicon photodiode as the photodetector.

LED light may be individually and periodically generated at each of the two or more wavelengths, to provide the component signal samples, taken, for example, at one second intervals. Each wavelength signal sample, the total duration of which may be about 5 milliseconds, may further comprise a rapid sequence of multiple, very brief LED illuminations, with very brief intervening periods of no generated light. By this process, the photodiode sensor can detect the net average signal value at each wavelength; i.e. total averaged illuminated signal, less the combined effect of the averaged circuit noise and ambient light samples, respectively. Computation of a PI value is achievable by subtracting a net signal value of the IR sample from a time-adjacent net red signal value.

In an infant intensive care monitor sensor embodiment, the PI sensor functions can be integrated with an adjunct reflectance $SpO_2$ monitoring function. This combination sensor can be further integrated with an adjunct electrocardiogram (ECG) signal detection system using multiple electrode skin contacts and electronic amplification, and graphically displayed together for clinical evaluation. The R-wave of a detected ECG signal can also be used to electronically create a timing trigger pulse for calculating the heart rate and beat-to-beat intervals for display and further analysis. The initialization and calibration cycle of the infant monitor system can also include determining the respective time delays from the R-wave trigger pulse to the following 'trough' and 'peak' in the continuous photoplethysmogram (PPG). Once these time intervals are determined, subsequent sampling of the IR and RED signals may occur only at the timed intervals of the 'trough' and 'peak' of each heart cycle. Thus, in the infant intensive care monitor embodiment, both the PI and the $SpO_2$ values can be continuously calculated from these two signal samples per heart cycle.

FIG. 1A illustrates a sensor 100 viewed from a skin contact side. The sensor 100 is a PI sensor which has a planar surface and a round form factor. Other shapes can be used without departing from the scope of the disclosure. A first LED 101 and a second LED 101' can communicate light to a subject's skin through a first housing aperture 102. The first LED and second LED are turned on separately. As will be appreciated by those skilled in the art, each LED could have a separate aperture, however, a single aperture as illustrated can also be used. A silicon photodiode 103 is visible through a second housing aperture 104. The housing of the sensor 100 has a skin contact plate 110, and a side wall 112. A connecting cable 120 can be provided. Alternatively, the sensor 100 can be in wireless communication with another device.

Figure 1B:
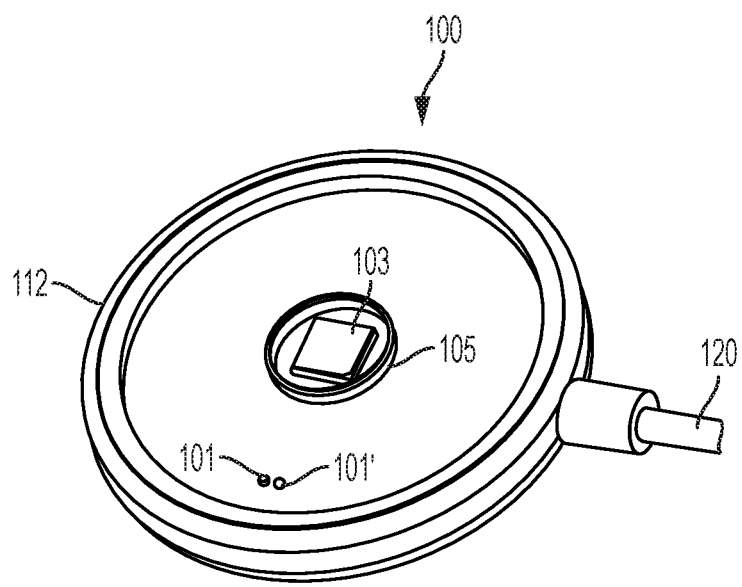
FIG. 1B shows the sensor with the aperture plate removed.

FIG. 1B illustrates the sensor 100 with the skin contact aperture plate 110 removed to show an embodiment of the optical physiologic sensor. Two LEDs 101, 101' are mounted beneath a first housing aperture 102. The silicon photodiode 103 is mounted beneath a second housing aperture 104. As illustrated, the first housing aperture 102 has a smaller area than the second housing aperture 104. Additionally, an 8 mm center-to-center offset can be provided between first housing aperture 102 and second housing aperture 104 in the skin contact aperture plate 110. The aperture plate can be made from any suitable material, including, for example, metal. An embodiment of the optical medium filling the apertures is optically clear epoxy, such as Epo-Tek P/N 301-2. The view in FIG. 1B shows the internal optical elements, plus an internal optical barrier 105, which is positioned to block internal light transmission between the emitters and the detector. The internal optical barrier 105 is configured as an interior wall with a circular shape. However, other barrier shapes can be used without departing from the scope of the disclosure. Additionally, power to operate the sensor can be provided to the sensor 100 via an internal power supply (such as a battery) or via an external power supply.

Figure 1C:
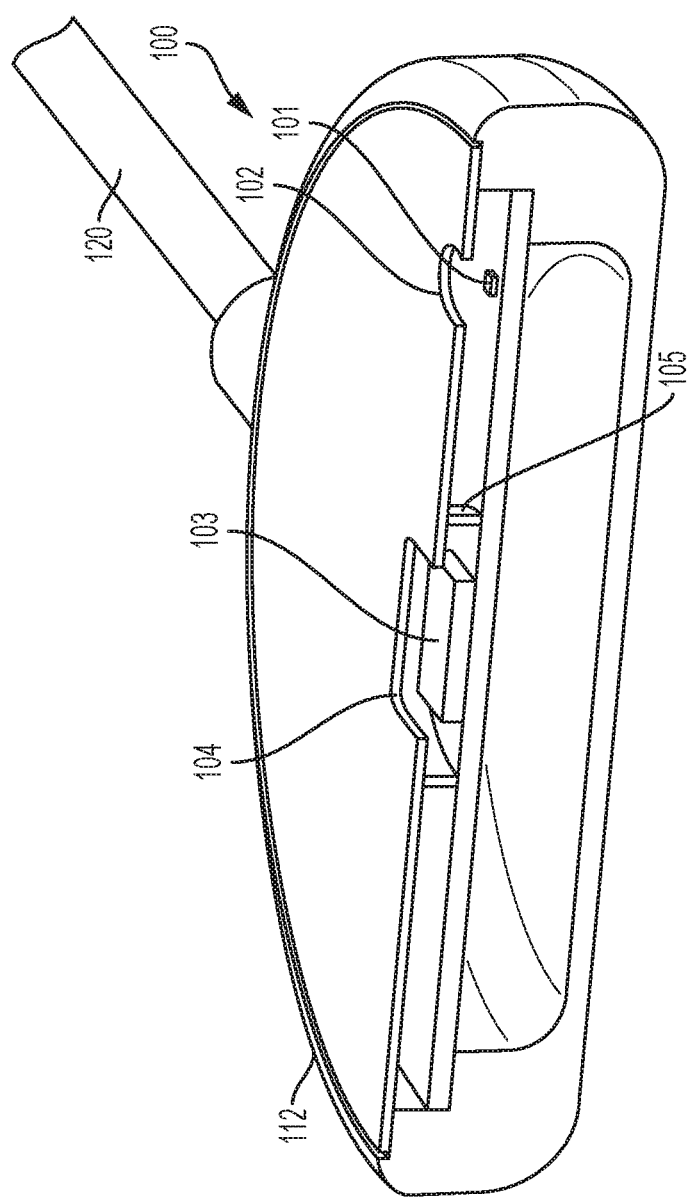
FIG. 1C is a cross-section of the sensor.

FIG. 1C is a cross-section of the sensor 100 with the LEDs mounted within the interior cavity of the sensor.

Figure 2A:
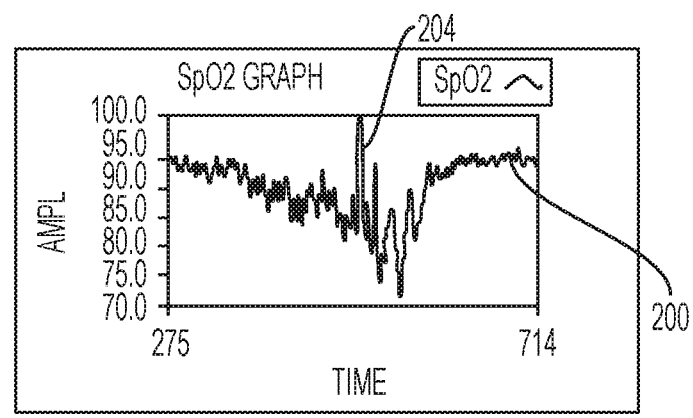
FIGS. 2A-B illustrate data recordings of the derived Physiologic Index (PI) using 660 nm and 810 nm during a hypoxia challenge test where the subject is breathing nitrogen-diluted air.
Figure 2B:
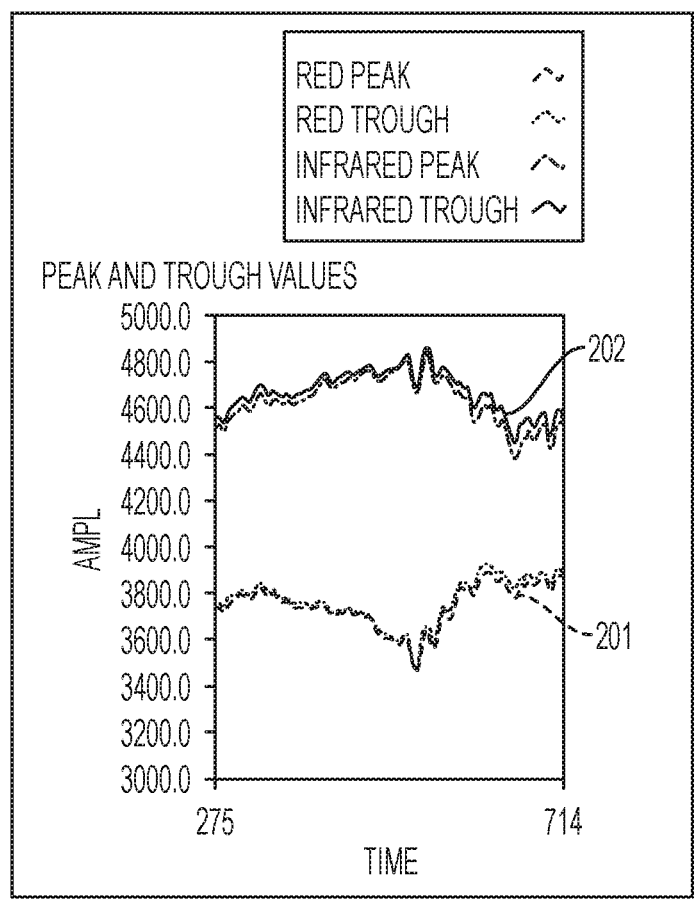

FIGS. 2A-B illustrate graphical recordings from an initial experiment using a sensor according to the disclosure. The recording illustrates that the DC (running average, or non-pulsatile) signal intensity measurements, then recorded using 660 nm 201 and 810 nm 202 LED light, consistently and uniquely vary coincidentally with decreasing blood hemoglobin-oxygen saturation as follows: (1) diffused light signal value of about 660 nm 201 (RED) light diverges from (2) the diffused light signal value of the about 810 nm (IR) light 202; i.e. the red signal intensity value decreases relative to the detected intensity value response of the IR signal with a hypoxic challenge. The disclosed PI value is derivable by subtraction of the net IR signal value from the net red signal value. Thus, during progressive tissue hypoxia, induced by briefly breathing nitrogen-($N_2$) diluted air via a non-rebreathing facemask, the PI value immediately, e.g. within 5 to 10 seconds, decreases to progressively more negative values; then rapidly returns to the initially calibrated "PI zero" baseline upon changing the breathing gas back to air.

FIG. 2A is a graph of calculated $SpO_2$ 200 based on the peak and trough values of the raw signal depicted by the graph in FIG. 2B. Of note is the very erratic $SpO_2$ trace 204 that was purposely disturbed by motion of the sensor vs. the skin of the subject to assess the effect of sensor motion. The $SpO_2$ calculation formula and conversion factor used was the same as was widely known in the medical device industry in January, 2000.

Figure 3A:
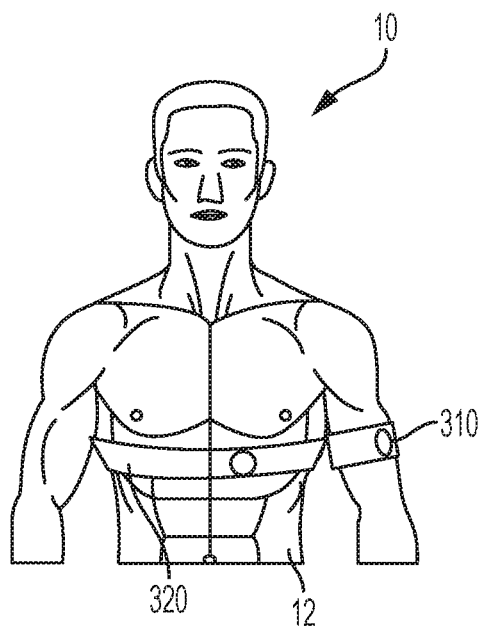
FIG. 3A illustrates placement locations for the disclosed sensor.

FIG. 3A depicts two suitable locations for the sensor on an adult subject 10. Placement of an arm sensor 310 on the upper arm of the subject 10 is convenient, comfortable, and leaves the wrists and hands of the subject free. A chest sensor 320 can be located on the chest 12 of a subject 10 and offers the possibility of integration with detection of ECG heart rate by use of skin contact electrode stickers and corresponding electronic circuitry and software.

Figure 3B:
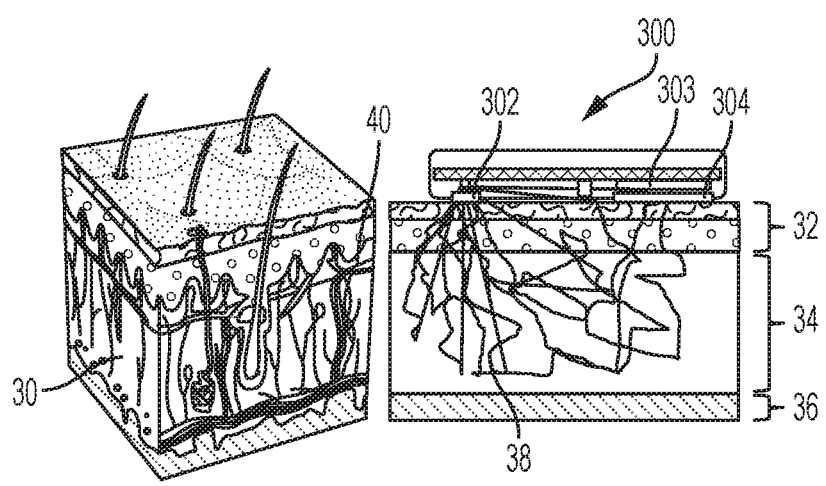
FIG. 3B illustrates differences between reflectance pulse oximetry ($SpO_2$) and the sensor on a skin surface.

FIG. 3B illustrates the anatomy of human skin 30 down to the hypodermis 36 next to a diagrammatic representation of the skin adjacent a sensor 300. The sensor 300 diffuses light 38 through the epidermis 32 and into the dermis 34 where it interacts with the various tissue elements and cellular chemical processes primarily above the hypodermis 36. Reflectance $SpO_2$, by contrast, selectively detects the very subtle pulsatile optical signal variations generated by the blood flowing in the dermal arterioles 40; using this phenomenon to produce an output value corresponding to the arterial blood hemoglobin oxygen saturation. By comparison, the disclosed sensor detects the non-pulsatile, bulk light that has diffused through the epidermis 32 and dermis 34 from the emitter aperture 302. Variations in the spectral optical density of this tissue space, as detected by the photodiode sensor 303 via the detector aperture 304 are the basis of the output PI signal, as disclosed herein.

Figure 4:
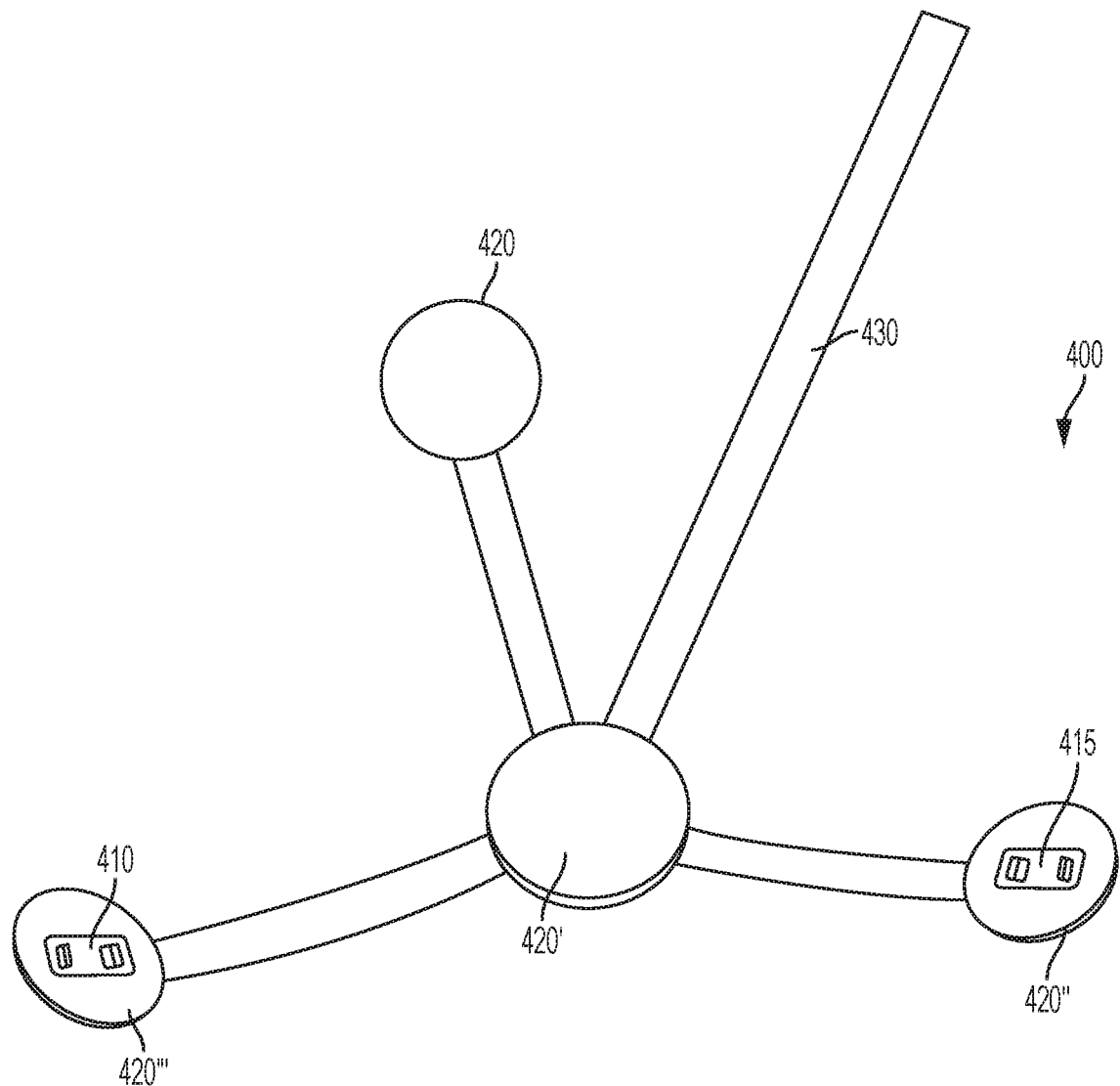
FIG. 4 illustrates an alternative embodiment having 2 sensors.

FIG. 4 illustrates an alternative embodiment of a sensor 400 suitable for use with premature newborn infants. Two sensors 410, 415 are used in this configuration. In use, a first sensor 415 is placed on the upper anterior right chest of the newborn and the second sensor 410 on the lower left abdomen of the newborn. Integrated with these two sensors 410, 415 are other contacts that, collectively, comprise one or more of: a 4-lead ECG, chest sound, and skin temperature measurement system 420, 420', which can connect to a headboard-mounted interface circuit via a connecting cable 430.

Figure 5:
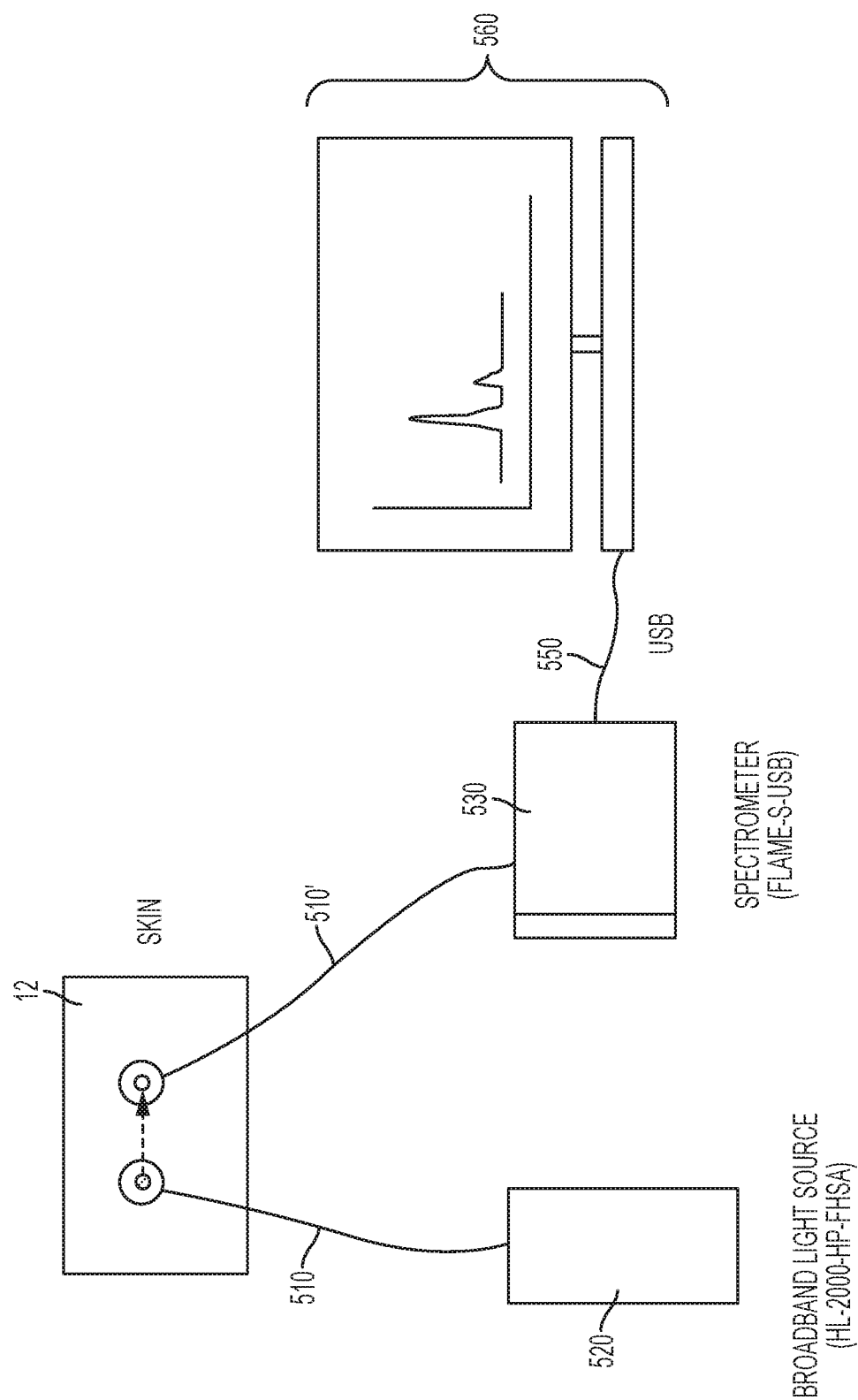
FIG. 5 illustrates an embodiment of the sensor using a lamp source and a spectrometer.

FIG. 5 schematically depicts an embodiment of a sensor system. In order to investigate the disclosed underlying biometric phenomenon in greater detail than is possible using fixed-center wavelength LEDs, a broadband quartz tungsten halogen (QTH) lamp light source 520 (HL-2000-HP-FHSA, Ocean Optics) is coupled to the skin 12 of a test subject with a fiber optic cable 510 (Thorlabs). Light that has diffused through the skin 12 is received and conveyed by a second fiber optic cable 510' to a spectrometer 530 (Flame-S-USB, Ocean Optics) for light detection and signal analysis. LabVIEW (National Instruments) software was used in a computer 560 to operate the lamp shutter, set the operating parameters of the spectrometer, and select the wavelength intensity values to be sampled and analyzed to produce a continuous reading and recording of the PI values. Recording with this spectrometer system, in parallel with a LED light-based prototype PI sensor, has produced very similar patterns of response, confirming, and validating previous and current observations, and demonstrating that the basis of the PI signal is closely associated with reproducible changes in the spectral optical density of the skin.

Figure 6A:
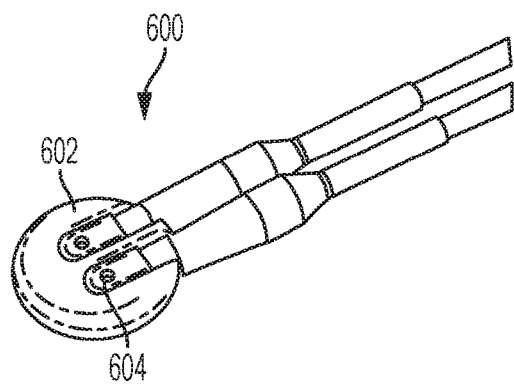
FIGS. 6A-C illustrate features of a skin contacting portion of a device configurable to place the ends of two optical fibers in optical contact with the skin.
Figure 6B:
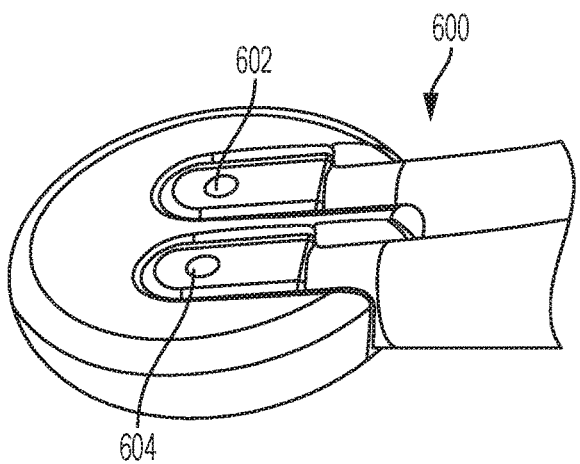

FIGS. 6A and 6B depicts the skin contact face of the fiber optic interface components of the spectrometer system in FIG. 5. Two apertures 602, 604 can be filled with a clear epoxy to convey light into and from the skin, respectively. One of the apertures 602 illuminates the skin, while the other aperture 604 receives the light that has diffused through the skin of the subject.

Figure 6C:
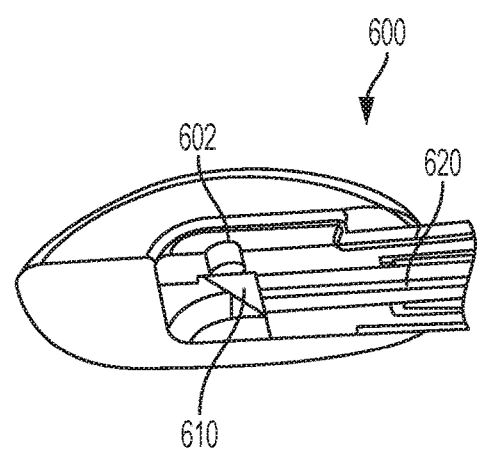

FIG. 6C is a cut view through the optical axis of one of the apertures, showing a silver-coated mirror 610 (Edmund Optics) in contact with the end of the optical fiber 620. The 90° reflected light is projected, or received through the respective housing aperture; spaced 8 mm on center.

Figure 7A:
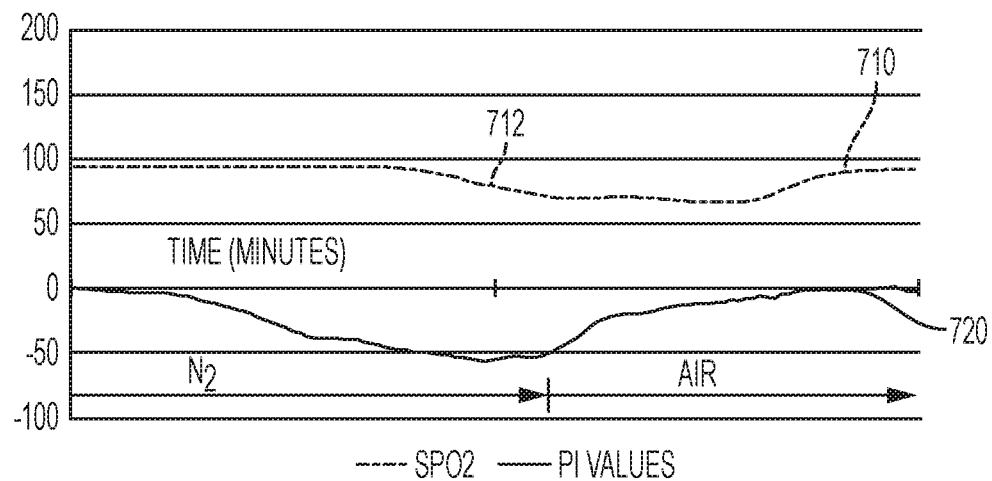
FIGS. 7A-B are line graphs of data recorded, and of a derived PI, using 660 nm and 850 nm light during a hypoxia challenge test wherein the subject is breathing nitrogen-diluted air.

FIG. 7A is a recording of a hypoxia challenge test using nitrogen gas delivered to the test subject via a non-rebreathing facemask. A medical transmission pulse oximeter (Masimo Radical 7) recorded the $SpO_2$ 710 via the subject's finger-tip during the test. The disclosed LED light-based PI sensor applied to the subject's upper arm produced the PI values of trace 720. Of note is the approximately 45 second delay 712 in the $SpO_2$ monitor's response to breathing nitrogen gas. By comparison, the PI signal value began to change within 10 seconds. The PI signal also registered the return to baseline prior to the response of the $SpO_2$ monitor.

Figure 7B:
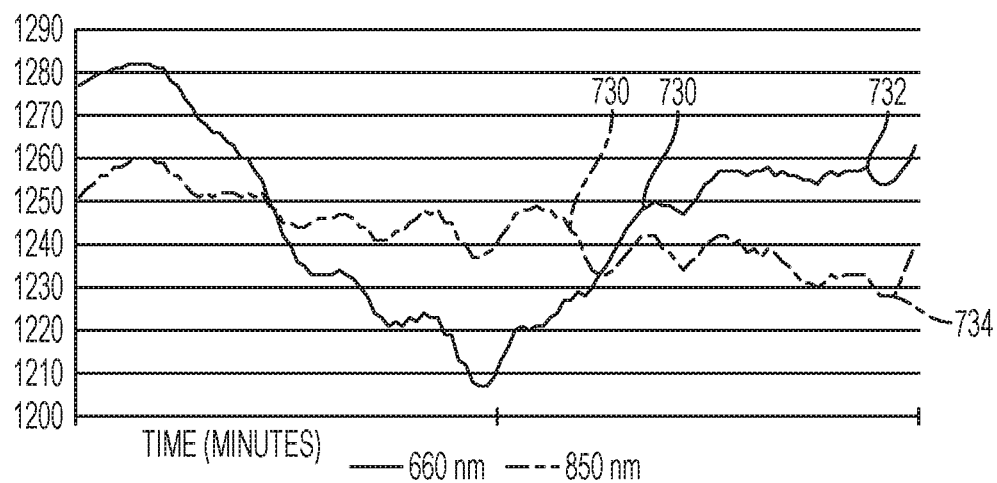

FIG. 7B is a line graph of the raw PI data from which the PI values in FIG. 7A were computed. The 850 nm signal line 734 remains less changed than the 660 nm signal line 732 throughout. It is their relative movement that is the basis of the computation of the PI values. Superimposed on both traces are variations 730 associated with the subject's normal breathing. Since the data samples are taken on timed one-second intervals, the appearance of heart cycle-induced pulsations is not seen.

Figure 8A:
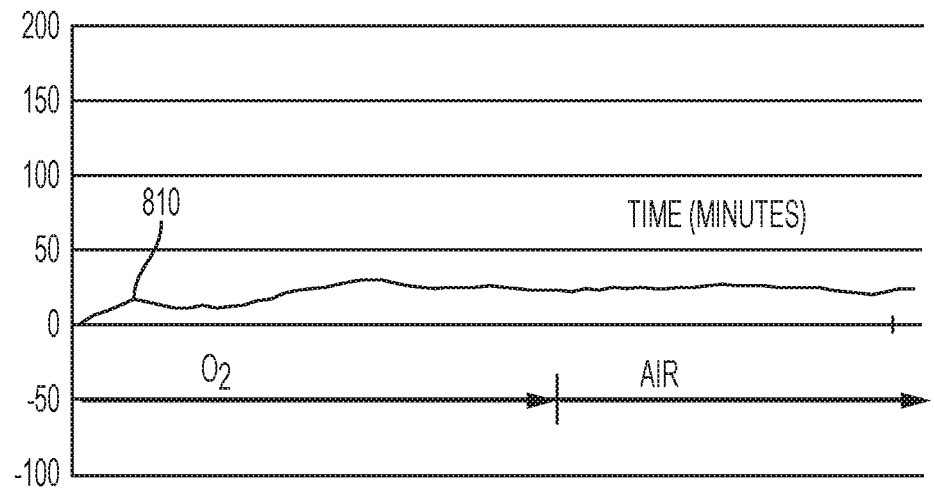
FIGS. 8A-B are line graphs of data recorded, and of a derived PI using 660 nm and 850 nm light during a hyperoxia challenge test where the subject is breathing pure oxygen.
Figure 8B:
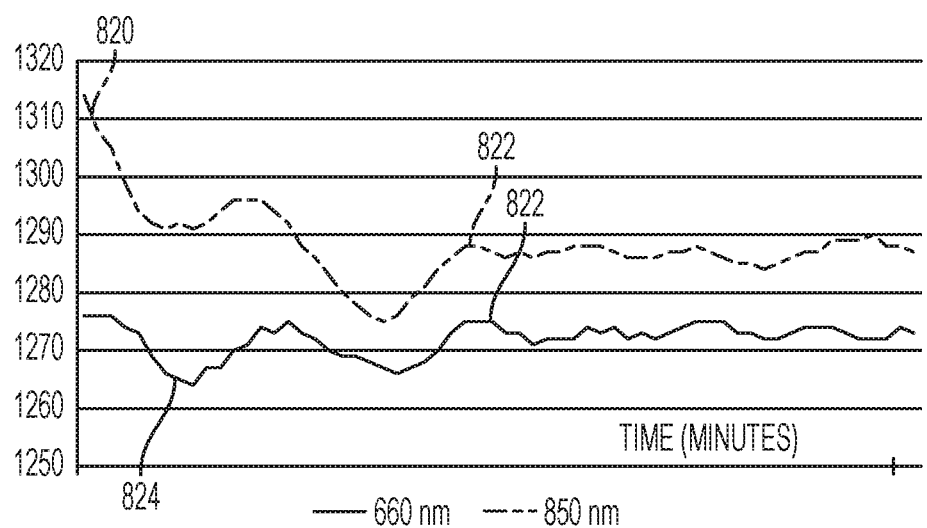

FIG. 8A is a recording of a hyperoxia challenge test using medical oxygen gas delivered to the test subject via a non-rebreathing facemask. As with the hypoxia challenge, the PI values 810 begin to change within 10 seconds, but, in this case, remain at an elevated value beyond the duration of the recording. FIG. 8B is the line graph of the raw PI data from which the PI values in FIG. 8A were computed. The 850 nm trace 820 responds quickly with a strong decreasing trend relative to the more constant 660 nm trace 824. Both traces also show breathing-induced fluctuations 822.

FIG. 9A is a combined recording of an exercise session using a heart rate monitor (Garmin) 910 and a $SmO_2$ monitor (Moxy) 920, 930. The heart rate is seen to rise in response to three, three-minute episodes of increased effort put forth by the test subject. There is also an increasing trend in the baseline heart rate due to a more gradually increasing baseline work load dialed into the exercise bicycle over the course of the session. The lower Moxy trace 930 shows the work load of the upper leg muscles, presenting this as the combination of arterial, capillary, and venous blood hemoglobin oxygen saturation within the muscle tissue. It is clear that the muscle extracts much of the oxygen during heavy work periods. The upper Moxy trace 920 shows the work load of the upper arm muscles, which is somewhat coincident, but less severely affected than that of the leg muscles.

FIG. 9B is the simultaneous recording of PI values 940. The initial six minutes appear to be aerobic, but the onset of the first and second sprints are clearly detected as a generalized body stress, since the PI sensor was placed on the subject's other upper arm. Of interest is a consistently observed upward trend 950 in PI baseline as the exercise session passes the about 20-minute mark. Even though the third sprint produces a higher heart rate, the PI trend descends only just below the baseline PI zero, then resumes a strong upward trend despite the exercise being discontinued 960.

FIG. 10A is the PI sensor record of a PI sensor system recording of an extended observation following a brief challenge 1000 with inhaled pure oxygen 1010.

FIG. 10B is the record produced in parallel by the spectrometer system 1020. This parallel recording test was performed to investigate how long the positive PI value persists and clearly shows that 15 minutes is not long enough to see even the beginnings of a returning-to-baseline trend. Despite a much more apparently "noisy" trace recorded by the spectrometer, the basic features of the PI value trend are seen in both recordings, confirming that the PI signal can be consistently obtained with at least two different instrument setups.

Figure 11:
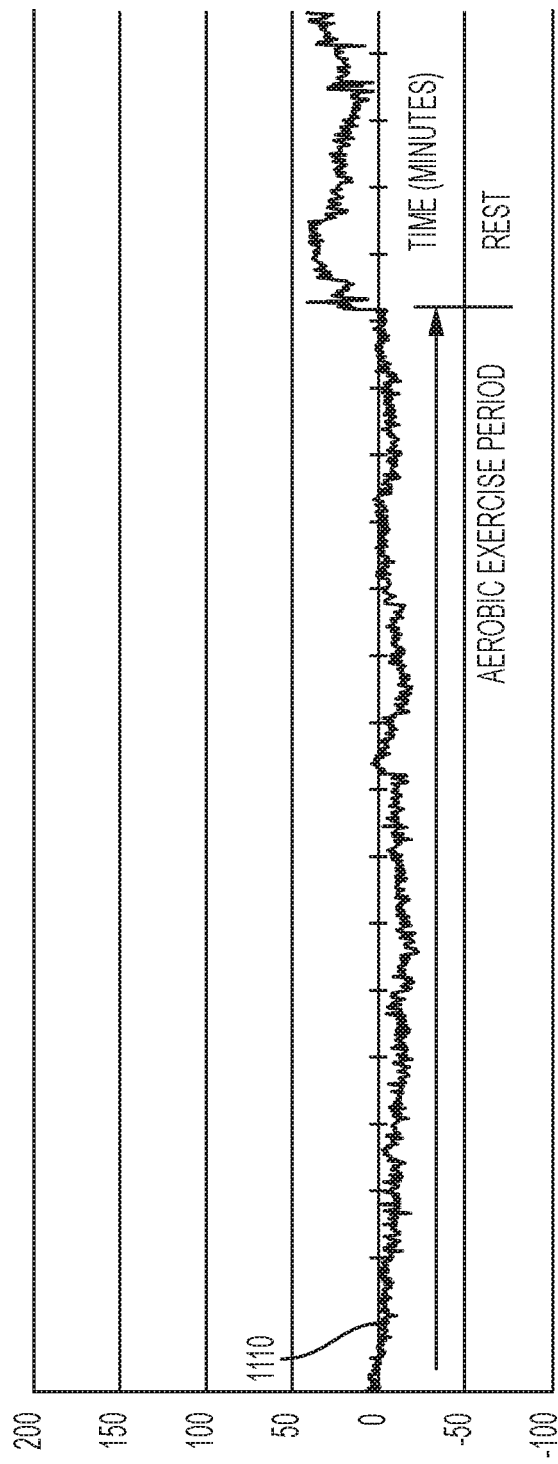
FIG. 11 is a line graph of data recorded using a QTH lamp light source and a spectrometer to obtain PI values during an exercise challenge test.

FIG. 11 is a spectrometer system-acquired exercise PI recording 1110 of an extended aerobic exercise bicycle session, which was abruptly stopped to investigate how high the PI value trend would go. This record does not show deep negative PI trend peaks as the athlete was asked to stay consistently at his sustainable work level.

Figure 12:
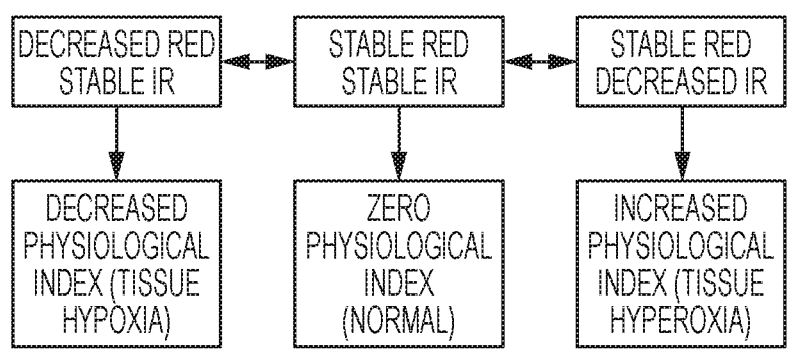
FIG. 12 illustrates the interrelationship of the three PI data phases.

FIG. 12 illustrates the interrelationship of the three PI data phases that have been recorded. Typically, a normal, healthy person at rest has, by definition, a "zero" PI. A continuous recording at rest has been observed to wander +/−5 points during moderate activity, such as standing or walking slowly for up to 5 minutes. PI has also been recorded during 2 hours of sitting and working with a computer at a desk; the results exhibited that there is a repeating pattern of a gradual positive drift of the PI value up to between 20 and 30 after 2 hours. This is expected to quickly return to the original baseline with standing or walking.

Within a few seconds of the onset of physical exertion, the PI value trend is typically negative; the downward rate of which is dependent upon the level of exertion. As exertion continues, and especially with intermittent bouts of extreme exertion, the PI data has consistently shown a gradual positive PI baseline value trend, which, in some subjects can rise into the 200 range after 20 to 30 minutes of exercise. There is a further increase in PI values upon suddenly stopping exertion after 30 minutes of heavy work. A positive trend of PI value up to about 40 has also seen with inhalation of oxygen. The positive trend seen at the end of exertion and after breathing oxygen have not been recorded long enough (only 15 minutes to date) to indicate the rate of return to the previous PI Zero level.

Figure 13:
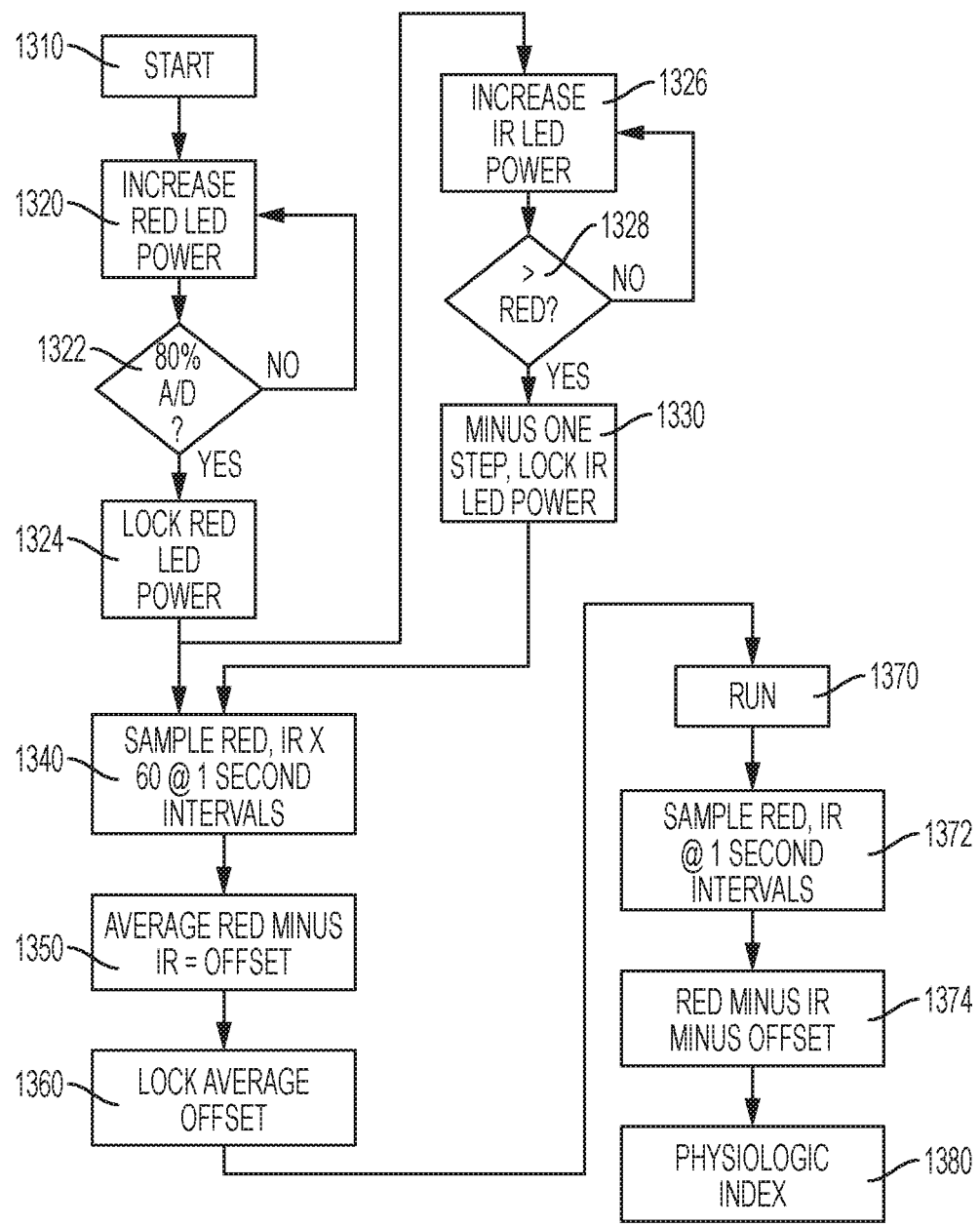
FIG. 13 outlines the initialization process of the PI sensor software.

FIG. 13 outlines the initialization process of the PI sensor software. Each subject, and each application site on a given subject, is expected to have differences in skin pigmentation and spectral optical density. These variations need to be accommodated to allow the sensor to center on the person's true PI zero. The process starts 1310 with increasing the RED LED power 1320 to a power level that places the resulting raw signal intensity at about 80% of the sensor A/D 1322 converter count range. The 80% value optimizes both the resolution of the sensor and accommodates potential increases in RED signal intensity that have been recorded to date. Once the RED LED power level has been determined and recorded in control memory the RED LED power is locked 1324, and the IR LED power level is similarly adjusted 1326 to just less than the signal intensity value detected with the RED LED at its locked power level 1328; and the IR LED power level is recorded and locked in control memory 1330.

Finally, prior to running the PI sensor, the average intensity offset value is determined over an initial one-minute period, with RED and IR samples taken at 1 second intervals 1340. The average signal offset bias (RED intensity minus IR intensity=offset bias) is then calculated 1350 and stored in control memory for use in subsequent calculations of the PI values 1360. Also included in all of these intensity samples is detection and subtraction of the ambient, or background, signal intensity that is a combination of the sensor circuit noise/bias and any ambient light that may be reaching the sensor.

The running process 1370 is enabled once the initialization process has completed, typically in a few seconds over one minute. After the run 1370 begins, the RED LED and IR LED are sampled at 1 second intervals 1372, the red minus IR offset is determined 1374 and a physiologic index is calculated 1380.

Figure 14:
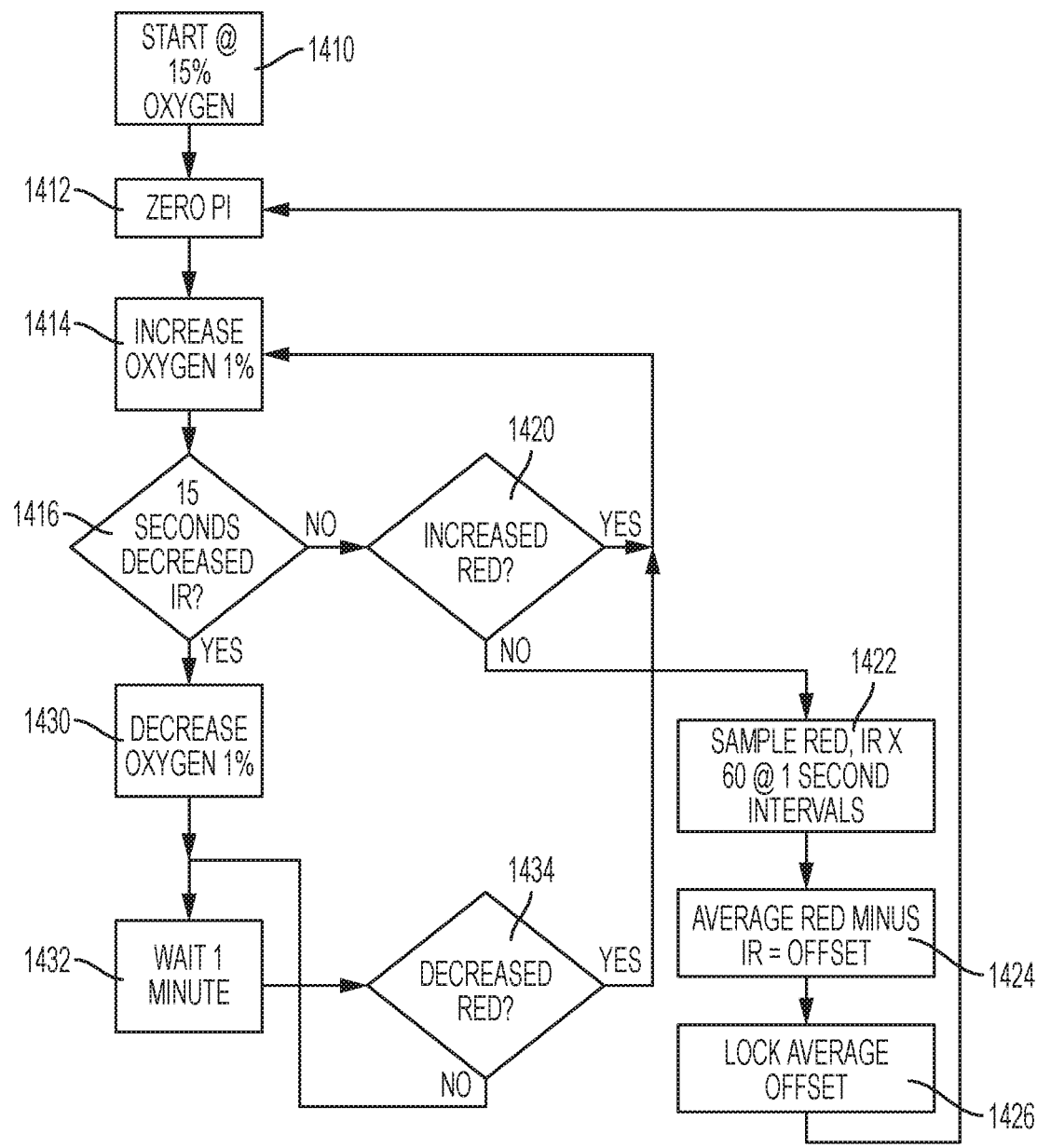
FIG. 14 outlines a proposed algorithm that could be used to regulate the breathing oxygen fraction delivered to monitored subjects.

FIG. 14 outlines an exemplar algorithm for use to regulate the breathing oxygen fraction of subjects, such as premature or distressed infants, who are born fully acclimated to the much lower tissue oxygen delivery rate of fetal life. It is also intended for use with other critically ill patients being resuscitated from prolonged ischemic or hypoxemic episodes, such as stroke, near drowning, suffocation, heart attack, or respiratory or cardiac arrest. It is assumed in all of these instances that the entire body of the patient, including the skin, will begin to receive supportive care at a lower than normal oxygen acclimation level. In the case of newborn infants, this level would be their prior fetal status, possibly lowered further by prolonged moderate stress, such as intrauterine growth restriction (IUGR), or by short term severe stress associated with the delivery. With non-newborns, the lower oxygen acclimation level is a result of natural adaptation reflex, life-sustaining responses by the autonomic nervous and cardiovascular systems under neural and endocrine control and, possibly, accompanied by down-regulation of intracellular antioxidant production and/or recycling.

In an effort to start with a tissue oxygen delivery rate that is less than harmful, some value of oxygen fraction less than atmospheric (20.8%) will likely be needed. This starting point will, ultimately, be determined empirically and will become a new part of the expert knowledge and judgment required of clinicians serving in this capacity. For illustrative purposes, the oxygen blend algorithm is started at 15% 1410 and then temporarily zero the PI 1412. From there, oxygen is increased in 1% increments 1414 depending upon the response of the PI sensor. Since recordings to date have shown a consistent response beginning at 5 seconds, and well established by 15 seconds, a suitable interval is 15 seconds 1416 which can be used as the iterative interval for updating the blend mechanism. Each initial 15 second cycle will test for the need to further increase the oxygen blend by 1%. This cycle continues up to the point where the IR intensity value begins to decrease 1416, signifying the onset of hyperoxia in the skin. At that point, the oxygen blend is reduced by 1% 1430 and the PI value is reviewed after one-minute 1432 to see if there is a need to move back up 1%. Thus, the system will tend to cycle +/−1% in oxygen fraction, while scanning for the need to either decrease or increase to accommodate the needs of the patient.

As this process plays out, there will come a point where neither the red nor the IR intensity values will change in response to a 1% change in oxygen fraction 1434, signifying that the subject's actual PI zero has been reached. At that point, a one-minute cycle of averaging the RED minus IR offset is performed to acquire a new offset value 1422, 1424, 1426; establishing an updated PI zero. This "re-zeroing" process will be indicated by the system display along with the current oxygen blend and the trend sequence of PI data values up to that point. No assumption is made as to the maximum level of oxygen fraction that will be needed; only that that fraction not result in a condition of skin tissue hyperoxia, or leave the patient in a state of skin tissue hypoxia. Ultimately, clinicians will need to determine when the proposed algorithm has established the patient's normal PI Zero.

Operation

When first applied to the skin, the disclosed sensor control runs an initial auto-ranging protocol. The initial auto-ranging protocol determines the signal levels at both wavelengths and then adjusts, in incremental steps of one or more of emitter power and detector amplifier gain, to maximize the resolution of analog-to-digital (A/D) conversion. Optimization is achieved when the two LED power levels and the corresponding light detector amplifier gain, produces diffused light DC digitized numerical values approaching, but not exceeding, about 80% of the maximum count limit of the A/D converter. This initialization process maximizes the resolution of A/D conversion, thus optimizing the accuracy of the computed PI (all users) and $SpO_2$ (infants only) values for each patient, helps compensate for differences in skin thickness and pigmentation, and allows a signal overhead range to accommodate the expected responses.

In the infant intensive care monitor embodiment, the full PPG signal is then analyzed for timing from the occurrence of a simultaneously obtained heart cycle-derived R-wave timing trigger pulse to the 'trough' and 'peak' PPG inflections. Each application site, and each subject being monitored, will likely have a unique time delay between the derived R-wave trigger pulse and the following 'trough' and 'peak' in the PPG optical signal. This variability in time intervals is due to the unique length and elasticity of the arterial pulse conduction pathway between the subject's heart and the sensor site. Once the automated adjustments have been completed, and the 'trough' and 'peak' sample timing intervals determined, the LED power levels, the detector amplifier gain level, and the sampling time intervals are recorded and locked as customized computation parameters in the control software. Thereafter, the computed oximetry is acquired and displayed, and the numerical difference between the two DC levels is continuously correlated with the computed oximetry to validate alarm status.

An additional safety feature may be enabled by PI analysis. In the event that a valid oximeter ensemble-averaging sample timing trigger cannot be obtained, such as commonly occurs when a monitored infant is crying, the PI value can be sampled on a default-timed basis. Obtaining diffused light levels on a clock-timed basis, such as once per second, will provide fully adequate data for the PI analysis and appropriate alarm generation. Further, in situations where heart rate and oximetry values have stabilized, as during quiet sleep, the default-timed mode may also be used as a significant sensor power conservation option in battery-supplied instruments.

An unexpected signal response was noted during an induced hypoxia challenge test of a prototype reflectance pulse oximeter for use on the chest and/or abdomen of newborn infants. Subsequent work has confirmed and refined this initial observation, revealing the potential for highly relevant new applications both in medical care and in the study of human physiology. The following explanations apply current knowledge of biochemistry and photonics as these disciplines apply to the study of human physiology and pathology. The methods, observations, and proposed explanations will, hopefully, be familiar and reasonable to students of undergraduate science and medical school, and who have, subsequently, observed and interacted with human physiology in health and disease.

Two main phenomena appear to be at play. First, skin tissue energy metabolism appears to be the main source of the variation in the photonic signals used to calculate PI. Factors likely causing variations in this metabolic chemistry, which apparently cause the resulting photonic responses, relate directly to the oxygen content of the blood delivered to the skin. This blood oxygen content is currently routinely monitored by pulse oximetry ($SpO_2$), and can be altered by breathing either nitrogen-diluted air, to reduce the $SpO_2$, or by breathing pure oxygen to exceed the blood oxygen saturation produced by breathing air; and observing the displayed data.

The second phenomenon appears to be independent of arterial blood oxygen content and relates to the autonomic nervous system's regulation of blood perfusion to skin tissue, both as a result of normal adaptation to stress, such as physical exercise and work, and pathologic, due to disease or injury-related processes. This blood perfusion regulation by the nervous system affects the process of energy conversion metabolism at the intracellular level in the skin. This influence is uniquely detected by the sensor due to the apparent accumulation of different molecules depending on whether insufficient oxygen (i.e. skin tissue hypoxia), or excess oxygen (i.e. skin tissue hyperoxia) is present.

Several areas of potentially significant clinical value of this new PI data relate to pathologic conditions known to decrease blood perfusion of the skin at the onset of the pathologic deterioration process. Such conditions as heart failure, resulting in decreased blood pumping capacity, and low circulating blood volume, such as due to blood loss from trauma or during surgery, trigger the autonomic nervous system to restrict blood perfusion of the skin as a life-protective reflex response. This reflex helps to maintain systemic blood pressure and conserves blood flow to preferentially serve the needs of more vital organs, such as the brain and heart. Likely the earliest sign of the onset of blood borne infection, or sepsis, is decrease in blood perfusion to the skin; again as a reflex response to maintain systemic blood pressure as the combination of bacterial toxins in the blood and the resulting immune system response causes relaxation of major blood vessels and a drop in blood pressure. Finally, there are several chronic health conditions, including chronic obstructive pulmonary disease (COPD), which tend to deteriorate at such a gradual rate that the patient may fail to discern the advancing stress and delay obtaining needed help until only heroic effort may suffice to preserve life and recover health. All of these conditions need a highly sensitive, conveniently wearable sensor that indicates the earliest pathologic changes, in order to signal for the initiation of needed intervention before the condition becomes dire; thus, improving quality of life and reducing cost and complexity of health care. $SpO_2$ monitoring technology is not currently "wearable" or convenient and does not adequately detect the skin perfusion reflex response seen early in sepsis and low blood volume, and early enough to be useful in detecting exacerbation of heart failure and COPD.

$SpO_2$ monitoring also does not detect potentially damaging excess oxygen at the tissue level, where it is toxic. Breathing gas with elevated partial pressure of oxygen can result in oxygen toxicity in the central nervous system, resulting in seizures. Occupations, recreational pursuits, and medical therapy where this may inadvertently occur include astronauts, high altitude pilots, SCUBA divers, and patients undergoing hyperbaric oxygen therapy.

Pathologies potentially caused by, or exacerbated by insufficient or excessive tissue oxygen are also a major concern with premature infants born earlier than about 30 weeks' gestation. Injuries include: retinal detachment and resulting impaired vision and even total blindness, brain hemorrhage, intestinal necrosis and perforation, cerebral palsy, and, most commonly, failure of the ductus arteriosus to close in a timely and complete fashion, resulting in an additional assortment of complications and life risks. Before birth, fetal blood oxygen saturation, and the resulting tissue oxygen level, are consistently very low compared to that of healthy full-term newborn infants, children, and adults. Due to the high efficiency of oxygen transport by fetal hemoglobin, fetuses actually thrive at this low tissue oxygen level and, unless they are born prematurely, continue to grow and develop normally and are at minimal risk of insufficient oxygen delivery-related injury. The current practice of intensive care is to regulate breathing oxygen blend according to the blood hemoglobin saturation, as indicated by blood gas sampling and $SpO_2$ monitoring, which cannot indicate whether the tissue oxygen delivery is less than, or more than, the tissue need. Thus, with blood oxygen monitoring only, potentially injuriously high (i.e. higher than fetal) tissue oxygen levels cannot be detected, and, thus, are currently not sufficiently avoidable. Current newborn resuscitation protocols using immediate administration of lung surfactant and appropriate ventilator treatment of premature lung disease have actually increased the risk of excessive tissue oxygen delivery during the infant's early transition from fetal placenta to breathing. With rapidly normalized lung function, even limiting the breathing gas oxygen level to atmospheric level (20.8%), either with assisted ventilation or spontaneous breathing, may still present an unacceptably high risk of vital tissue injury due to excess tissue oxygen delivery, compared to the relatively very low tissue oxygen delivery during fetal life. Thus, there is a combined need for accurate, continuous monitoring of the adequacy of tissue oxygen delivery, coupled with automatically-regulated, initially lower-than-atmospheric fraction of oxygen in the breathing gas for the resuscitation and early management of these very vulnerable infants as they make their transition from fetal to air-breathing life. Continuously knowing the skin tissue-level oxygen metabolic status relative to skin tissue metabolic need for oxygen, as a surrogate index for vital organs, has long been a recognized and critical, but unmet, need of premature infant health care. The PI sensor described herein offers a potentially viable source of this critical information. Applied to the skin of the premature infant immediately following birth, the PI sensor's "find PI zero" algorithm can be used to guide the automated regulation of the oxygen/nitrogen blend of the breathing gas mixture, beginning at a less-than atmospheric oxygen fraction, such as at about 15%. Then, periodic, small step increases in the breathing gas oxygen fraction can be made until PI zero is encountered, whereupon the breathing gas oxygen fraction can be continuously and automatically adjusted to maintain skin tissue oxygen delivery to maintain a near-zero PI value, as a surrogate of oxygen delivery to vital organs. Thus, each individual premature infant patient can be objectively managed on a unique, automated timeline of adaptation toward breathing atmospheric air, or higher oxygen fraction if needed, then weaned to atmospheric oxygen levels as the lungs mature and heal. The ultimate goal is to reduce the incidence of the devastating injuries that can be caused by either inadequate or excess oxygen delivery to the extremely fragile and immature brain, gut and vascular tissues of these infants.

The systems and methods according to aspects of the disclosed subject matter may utilize a variety of computer and computing systems, communications devices, networks and/or digital/logic devices for operation. Each may, in turn, be configurable to utilize a suitable computing device which can be manufactured with, loaded with and/or fetch from some storage device, and then execute, instructions that cause the computing device to perform a method according to aspects of the disclosed subject matter.

A computing device can include without limitation a mobile user device such as a mobile phone, a smart phone and a cellular phone, a personal digital assistant ("PDA"), such as an iPhone®, a tablet, a laptop, and the like. In at least some configurations, a user can execute a browser application over a network, such as the Internet, to view and interact with digital content, such as screen displays. A display includes, for example, an interface that allows a visual presentation of data from a computing device. Access could be over or partially over other forms of computing and/or communications networks. A user may access a web-browser, e.g., to provide access to applications and data and other content located on a web-site or a web-page of a web-site.

A suitable computing device may include a processor to perform logic and other computing operations, e.g., a stand-alone computer processing unit ("CPU"), or hard wired logic as in a microcontroller, or a combination of both, and may execute instructions according to its operating system and the instructions to perform the steps of the method, or elements of the process. The user's computing device may be part of a network of computing devices and the methods of the disclosed subject matter may be performed by different computing devices associated with the network, perhaps in different physical locations, cooperating or otherwise interacting to perform a disclosed method. For example, a user's portable computing device may run an app alone or in conjunction with a remote computing device, such as a server on the Internet. For purposes of the present application, the term "computing device" includes any and all of the above discussed logic circuitry, communications devices and digital processing capabilities or combinations of these.

Certain embodiments of the disclosed subject matter may be described for illustrative purposes as steps of a method which may be executed on a computing device executing software. Included are software program code/instructions that can be provided to the computing device or at least abbreviated statements of the functionalities and operations performed by the computing device in executing the instructions. Some possible alternate implementation may involve the function, functionalities and operations occurring out of the order, including occurring simultaneously or nearly so, or in another order or not occurring at all. Aspects of the disclosed subject matter may be implemented in parallel or seriatim in hardware, firmware, software, or any combination(s) of these, co-located or remotely located, at least in part, from each other, e.g., in arrays or networks of computing devices, over interconnected networks, including the internet, and the like.

The instructions may be stored on a suitable "machine readable medium" within a computing device or in communication with or otherwise accessible to the computing device. As used in the present application a machine-readable medium is a tangible storage device and the instructions are stored in a non-transitory way. At the same time, during operation, the instructions may at some times be transitory, e.g., in transit from a remote storage device to a computing device over a communication link. However, when the machine readable medium is tangible and non-transitory, the instructions will be stored, for at least some period of time, in a memory storage device, such as a random access memory (RAM), read only memory (ROM), a magnetic or optical disc storage device, or the like, arrays and/or combinations of which may form a local cache memory, e.g., residing on a processor integrated circuit, a local main memory, e.g., housed within an enclosure for a processor of a computing device, a local electronic or disc hard drive, a remote storage location connected to a local server or a remote server access over a network, or the like. When so stored, the software will constitute a "machine readable medium," that is both tangible and stores the instructions in a non-transitory form. At a minimum, therefore, the machine readable medium storing instructions for execution on an associated computing device will be "tangible" and "non-transitory" at the time of execution of instructions by a processor of a computing device and when the instructions are being stored for subsequent access by a computing device.

EXAMPLES

Sepsis

Another example of an application of the disclosed technology is directed to an alternative process for continuous re-evaluation and adjustment of the PI zero. Many potentially useful applications of the disclosed apparatus and methods will start when the monitored subject is not in a healthy, resting state. For example, at the initial presentation of a patient with early sepsis to a hospital emergency department, there is likely already a significant pathologic decrease of the blood perfusion to the skin, resulting in the skin tissue status being within the person's previous anaerobic range; i.e. negative PI value. Simply using the presenting abnormal physiologic conditions to set the PI zero will result in an indeterminate negative deviation of the PI zero relative to that person's previous healthy, resting PI zero. As effective treatment is administered, and the patient's physiologic status improves back toward normal health, the transition between negative PI and positive PI values, i.e. the PI zero, will migrate upward until it stabilizes at the patient's true normal level. To continuously monitor and adapt to movement of this transition, a "finding PI zero" algorithm can be applied, whereby the relative changes of the red and IR intensity signals are used to repeatedly determine when the current PI value crosses the transition; i.e. the actual PI zero. For example, if the IR signal is unchanged, but the red signal progressively increases in value as a result of effective therapy, the subject is currently still in the negative PI range, but is approaching PI zero. As the physiologic condition continues to improve toward normal, a new PI zero will be defined as: 'when the red signal value becomes stable, while the IR signal begins to decrease in value.' As this transition is detected, the fixed bias value will be updated to the current offset between the red and IR signal values, bringing the calculated PI value to the updated zero.

Premature Infants

As another example, moments before birth, a premature newborn infant will be fully acclimated to the much lower fetal blood oxygen saturation ranging from as low as about 10% up to as high as about 60%, with corresponding relatively low fetal tissue oxygen delivery rate, relative to the eventual rate of oxygen delivery to tissue during air-breathing life. Current medical practice uses "blood gas" ($SaO_2$) measurements of the newborn infant's arterial blood and pulse oximetry ($SpO_2$) measurements to guide the oxygen fraction blending of breathing gas during initial care of premature infants following birth. Monitoring of skin tissue oxygen tension, using a Clark electrode sensor, is also an accepted way of guiding oxygen delivery in the medical care of premature infants. Most recently, use of infrared light has enabled non-invasive measurement of the hemoglobin/ oxygen saturation of the combination of arterial, capillary, and venous blood deep within the infant's brain, as an index of the adequacy of blood perfusion and oxygen delivery to the brain. The guiding assumption with the use of these instruments and associated current practices, is that low blood oxygen (hypoxemia) and resulting low tissue oxygen level (tissue hypoxia), is the root cause of the unique and devastating vital organ tissue injuries encountered by premature infants. However, current research literature is reporting that the initial injury that occurs in these tissues is to the endothelial cells lining the post-capillary venules. Also recently reported is that these injuries are directly associated with an abrupt onset of a relatively excessive oxygen delivery rate. Death and disintegration of these venule endothelial cells triggers blood clotting and results in blockage of blood flow through their respective capillaries and, ultimately, the death of the tissues supplied by those capillaries. Unfortunately, blood oxygen measurements cannot indicate when the oxygen delivery rate exceeds the tolerance level of these very sensitive endothelial cells. Assuming normal lung function is rapidly established as a result of immediate treatment using lung surfactant, breathing normal 20.8% oxygen fraction air has been consistently observed to raise the infant's arterial blood oxygen saturation above 80%, or even as high as 90%, which is far higher than ever occurs with fetal blood from the placenta. Aggravating this situation is the known lower production of tissue-protective antioxidants, such as glutathione, in infants less than about 30 weeks' gestation. Thus, with less than adequate tissue antioxidant protection, these infants are at risk of suffering hyperoxic injury to the microvascular endothelium in the brain, gut, and eyes when these organs are suddenly perfused with much higher oxygen content blood, compared with the fetal environment moments before birth. Until the discovery of the PI signal, there has been no method of detecting when tissues are receiving less than enough oxygen, just the right amount of oxygen, or too much oxygen relative to their current need and capacity to safely utilize oxygen.

Newborns

In a similar example with premature infants, the full gestation infant's initial PI zero is also expected to start at a lower blood oxygen level than it will transition to become when the infant's tissues have had time to adapt to the higher oxygen availability of air-breathing life. In the case of full-term infants in distress from a variety of complications of birth, the infant's breathing gas may also be more safely started with a sub-atmospheric oxygen fraction, such as 15%. Then, as the infant's tissue oxygen need and oxygen tolerance gradually increases, the PI monitor may provide a surrogate index for vital organ oxygen need and tolerance. It is anticipated that early evidence of this adaptation will be seen when the red signal intensity begins to decrease relative to a stable IR signal intensity, indicating the need for an increase in the oxygen fraction in the breathing air until the red signal remains stable, and the IR signal level begins to decrease; thus identifying the new PI zero. A new fixed offset value will then be established, defining this updated PI zero. Note that these determinations and breathing gas oxygen fraction changes are essentially independent of the infant's arterial blood hemoglobin/oxygen saturation level. Blood oxygen measurements relate only to the efficiency of the lungs and blood as oxygen transport agents and cannot specifically indicate whether vital organ tissues are being safely and effectively supplied with oxygen. The tissue injuries, especially those caused by an excessive rate of tissue oxygen delivery, occur in the vital organs of newborn infants, and not in their blood. The disclosed PI monitoring apparatus and method, coupled with the PI monitoring-enabled regulation of breathing oxygen fraction disclosed herein, present a potentially safer and more effective initial care process compared with guidance based on blood oxygen metrics.

Exercise

Still another aspect of the disclosure is directed to physiologic sensors that are configured to detect, using two-, or multi-wavelength photonic signal variation, a skin microcirculatory and/or skin tissue metabolic chemistry response to muscular exertion, such as occurs with recreational exercise, weight loss exercise, athletic training and performance, or occupational work, etc.; as a surrogate index for the total body physiologic load presented by the muscular activity. Additionally, the disclosed sensors can be configured to show the observed PI signal baseline shift response pattern thought to indicate the rate of onset of fatigue apparently associated with the combination of the extent of mechanical work output and the duration of the exertion. Current research relative to exercise regimens designed for athletic training, general health maintenance, rehabilitation following injury or surgery, and obesity weight loss, advocates the need for exercise sessions to be accurately designed for each individual such that the exercise can be both safe and effective in achieving the desired goals. The new physiologic information provided by the disclosed PI sensors can be used to help optimize individual exercise regimens toward achieving the safety and performance goals. As an example, the beginning phase of a weight-loss oriented exercise regimen designed for a 300-pound person in precarious health needs to initially use low-impact exercise and minimize stress to the heart, so as to not injure major weight-bearing joints or trigger a heart attack. At the same time, however, the exercise regimen needs to measurably improve general health status and achieve an efficient rate of loss of stored body fat as a result of the person's investment in time, effort, emotional stress, and economic cost. The work load progression, exercise session duration, and session repetition timing for such a person will also need to accommodate individual preferences, or it risks not being sustainable. Today's therapist/trainers must substitute experience-based expert opinion for needed, but missing, objective measurements of tissue-level physiology. Theoretically, based on current research data, using stored body fat as the major fuel source for a weight loss exercise regimen calls for extended, purely aerobic-level exertion, rather than multiple brief bouts of heavy work to exhaustion. Finally, the exercise regimen needs to generate the biological signal/s that will up-regulate the production of tissue enzyme systems needed to prepare body fat for energy conversion. Further, sufficient rest and recovery time needs to be allowed prior to the next episode to fully capitalize on the stimulated gains. Currently, return to baseline resting heart rate, and return to baseline beat-to-beat heart rate variability upon waking in the morning, are used to gauge recovery from exercise. While these population statistics-derived indices may reflect heart health, the newly discovered PI signal provides an objective, potentially more relevant, individualized view of energy conversion chemistry, as a surrogate index of this process throughout the body. The sufficient recovery period for each person could, as an example, be determined by evaluating their rate of PI value fatigue trend at their next exercise session; with a more rapid PI baseline rise indicating insufficient recovery. Until the discovery of the PI signal, there has not been a convenient, non-invasive, objective method of indicating that a person is: (1) exercising within their aerobic window, (2) that at the end of each exercise session there is an effective biological signal generated that will up-regulate fat utilization enzyme processes, and (3) that sufficient recovery time has elapsed before another session.

Hypothermia

In still another aspect of the disclosure, diffused light physiologic sensors are described that detect, by two-, or multi-wavelength photonic signal variation, the skin microcirculatory and/or skin tissue chemical reaction response to adverse conditions, such as hypothermia from cold exposure, progressive hyperthermia from excessive environmental temperature/humidity exposure, or adverse reaction to infused or ingested pharmacologic chemicals, such as when anesthetic or other pharmacologic or other potentially, or actually toxic agents have been introduced into the body, and during recovery from such conditions, influences and reactions; as a surrogate index of reflex responses protective of vital organ tissues.

Tissue Ischemia

Additional aspects of the disclosure include physiologic sensors that are configurable to detect, by two-, or multi-wavelength photonic signal variation, the tissue microcirculatory and/or tissue chemical reaction response during re-perfusion following tissue ischemia, such as is purposefully used during orthopedic surgery to achieve a bloodless surgical field, or, in general, as happens with return of blood perfusion to body parts or organs that have been temporarily under-perfused, or not perfused; for the purpose of monitoring that the amount of oxygen delivered by the circulating blood to the re-perfused tissue does not exceed that tissue's temporarily diminished, and gradually recovering, capacity to utilize the delivered oxygen; thereby helping to optimize therapy. Related examples could include resuscitation and recovery from central nervous system ischemic stroke and resuscitation following prolonged episodes of hypoxemia due to suffocation, near-drowning, cardiac and/or respiratory arrest. Current therapy often includes a period of induced total body cooling, or hypothermia and/or pharmacologic-induced coma, to slow the metabolism of the brain. The remarkable success of hypothermia and induced coma therapies indicates, among other factors, that the most sensitive tissues in the brain can survive relatively long periods at lower oxygen levels, but need time to up-regulate their capacity to utilize and tolerate delivery of oxygen at normal $SpO_2$ and perfusion levels. For example, since the less vital body tissues, such as the bones, muscles, and skin, more easily tolerate lowered oxygen delivery, the breathing gas oxygen fraction could be lowered gradually, with cardiac monitoring, to bring the patient's $SpO_2$ down to the 65-70% range for about 30 minutes. This would allow the skin to acclimate to the lower level of oxygen supply, as it has been recorded to do by recording PI sensor data during periods of exercise. This skin acclimation process is also a normal part of adapting to living at a higher altitude. As this acclimation occurs, the "finding PI zero" algorithm will re-establish PI zero at the lower $SpO_2$ level. Then, since the skin serves as a perfusion buffer to more vital organs, it may be monitored as a surrogate of more vital organs, with the PI sensor used to guide the gradual upward adjustment of the oxygen fraction in the breathing gas. Theoretically, if organs more vital than the skin begin to need increased amounts of oxygen, the skin will become more anaerobic as the autonomic nervous system diverts skin perfusion to these more vital organs, as it does during exercise and septic shock. Thus, when the PI value goes more negative, indicating perfusion diversion to more vital organs, the breathing oxygen fraction can be increased to bring the PI value back up to zero; and this cycle repeated until the person is breathing atmospheric oxygen fraction.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A physiologic index sensor comprising:
   a first means for emitting a first wavelength wherein the first means for emitting the first wavelength is configurable to emit a first target wavelength of from 650 nm to 670 nm into an epidermis layer and a dermis layer of a user;
   a second means for emitting a second wavelength wherein the second means for emitting the second wavelength is configurable to emit a second target wavelength of from 840 nm to 860 nm into the epidermis layer and the dermis layer of the user;
   a detection means optically isolated from the first means for emitting the first wavelength and the second means for emitting the second wavelength wherein the detection means is configured to detect a first diffused wavelength and a second diffused wavelength;
   a processor means configured to perform an initialization process to determine a a second power level of the second means for emitting a second wavelength having a second detected signal intensity less than the first detected signal intensity;
   subsequently operate the first means for emitting and the second means for emitting at the first power level and the second power level, respectively, and receive an input from the detection means;
   further wherein the processor means is configured to calculate an oxygen-related energy conversion metabolism from the input and determine a tissue oxygen requirement; and
   a power source.

2. The physiologic index sensor of claim 1 wherein the physiologic index sensor further comprises a data transmitter means.

3. The physiologic index sensor of claim 1 wherein the physiologic index sensor is configurable to determine one or more of an index of oxygen delivery and aerobic energy conversion.

4. The physiologic index sensor of claim 1 further comprising a housing means having a first aperture and a second aperture.

5. The physiologic index sensor of claim 4 wherein the first aperture and the second aperture are filled with an optically clear material.

6. The physiologic index sensor of claim 4 further comprising a securer means configured to secure the physiologic index sensor to an arm or a chest of the user.

7. The physiologic index sensor of claim 1 further comprising one or more electrically conductive skin contact adhesive means.

8. The physiologic index sensor of claim 1 wherein at least one of the first means for emitting the first wavelength and the second means for emitting the second wavelength is connected to a physiologic index sensor housing via a cable.

9. The physiologic index sensor of claim 1 wherein at least one of the first means for emitting the first wavelength and the second means for emitting the second wavelength is an unfiltered broadband light source, using optical fiber cables for light conveyance to and from the skin, and the detection means is a spectrometer, with selected wavelength intensity values obtained by the spectrometer used to compute the physiologic index.

10. A physiologic index sensor comprising:
a first emitter for emitting a first wavelength wherein the first emitter for emitting the first wavelength is configurable to emit a first target wavelength of from 650 nm to 670 nm into an epidermis layer and a dermis layer of a user;
a second emitter for emitting a second wavelength wherein the second emitter for emitting the second wavelength is configurable to emit a second target wavelength of from 840 nm to 860 nm into the epidermis layer and the dermis layer of the user;
a detector optically isolated from the first emitter and the second emitter wherein the detector is configured to detect a first diffused wavelength and a second diffused wavelength;
a processor configured to perform an initialization process to determine first power level of the first emitter having a first detected signal intensity of about 80% of a sensor system A/D converted maximum count limit and a second power level of the second emitter having a second detected signal intensity less than the first detected signal intensity;
subsequently operate the first emitter and the second emitter at the first power level and the second power level respectively, and receive an input from the detector wherein the processor is configured to calculate an oxygen-related energy conversion metabolism from the input and determine a tissue oxygen requirement, and;
a power source.

11. The physiologic index sensor of claim 10 wherein the physiologic index sensor further comprises a data transmitter.

12. The physiologic index sensor of claim 10 wherein the physiologic index sensor is configurable to determine one or more of an index of oxygen delivery and aerobic energy conversion.

13. The physiologic index sensor of claim 10 further comprising a housing having a first aperture and a second aperture.

14. The physiologic index sensor of claim 13 wherein the first aperture and the second aperture are filled with an optically clear material.

15. The physiologic index sensor of claim 13 further comprising a securer configured to secure the physiologic index sensor to an arm or a chest of the user.

16. The physiologic index sensor of claim 10 further comprising one or more electrically conductive skin contact adhesive pads.

17. The physiologic index sensor of claim 10 wherein at least one of the first emitter for emitting the first wavelength and the second emitter for emitting the second wavelength is connected to a physiologic index sensor housing via a cable.

18. The physiologic index sensor of claim 10 wherein at least one of the first emitter for emitting the first wavelength and the second emitter for emitting the second wavelength is an unfiltered broadband light source, with two or more wavelength intensity values being selected by a spectrometer to be used to compute a physiologic index value.

19. A physiologic index sensor comprising:
a housing adapted to engage a chest or an arm of a user wherein the housing has a first aperture and a second aperture;
a first emitter wherein the first emitter is configurable to emit a first wavelength through the first aperture into an epidermis layer and a dermis layer of the user;
a second emitter wherein the second emitter is configurable to emit a second wavelength through the first aperture into the epidermis layer and the dermis layer of the user;
a detector disposed within the housing wherein the detector is optically isolated in the housing from the first emitter and the second emitter and adjacent the second aperture and further wherein the detector is configured to detect a first wavelength diffused through the epidermis layer and the dermis layer and a second wavelength diffused through the epidermis layer and the dermis layer;
a processor configured to perform an initialization process to determine a first power level of the first emitter having a first detected signal intensity of about 80% of a sensor system A/D converted maximum count limit and a second power level of the second emitter having a second detected signal intensity less than the first detected signal intensity;
subsequently operate the first emitter and the second emitter at the first power level and the second power level, respectively, and receive an input from the detector wherein the processor is configured to calculate an oxygen-related energy conversion metabolism from the input and determine a tissue oxygen requirement; and
a power source.

20. The physiologic index sensor of claim 19 wherein the physiologic index sensor further comprises a data transmitter.

21. The physiologic index sensor of claim 19 wherein the physiologic index sensor is configurable to determine one or more of an index of oxygen delivery and aerobic energy conversion.

22. The physiologic index sensor of claim 19 wherein the first aperture and the second aperture are filled with an optically clear material.

23. The physiologic index sensor of claim 19 further comprising a securer configured to secure the physiologic index sensor to the arm or the chest of the user.

24. The physiologic index sensor of claim 19 wherein at least one of the first emitter for emitting the first wavelength and the second emitter for emitting the second wavelength is connected to a physiologic index sensor housing via a cable.

25. The physiologic index sensor of claim 19 wherein at least one of the first emitter for emitting the first wavelength and the second emitter for emitting the second wavelength is an unfiltered broadband light source, with two or more wavelength intensity values being selected by a spectrometer to be used to compute a physiologic index value.

26. A method of detecting a biological parameter comprising:
placing a physiologic index sensor adapted to be in contact with an arm or a chest of a patient wherein the physiologic index sensor further comprises, a first emitter for emitting a first wavelength into an epidermis layer and a dermis layer of a user wherein the first emitter for emitting the first wavelength is configurable to emit a first target wavelength of from 650 nm to 670 nm, a second emitter for emitting a second wavelength into the epidermis layer and the dermis layer of the user wherein the second emitter for emitting the second wavelength is configurable to emit a second target wavelength of from 840 nm to 860 nm, a detector optically isolated from the first emitter and the second emitter wherein the detector is configured to detect a first wavelength diffused through the epidermis layer and the dermis layer of the user and a second wavelength diffused through the epidermis layer and the dermis layer of the user, a processor configured to receive an input from the detector;
powering the physiologic index sensor with the power supply;
performing an initialization process to determine a first power level of the first emitter having a first detected signal intensity of about 80% of a sensor system A/D converted maximum count limit and a second power level of the second emitter having a second detected signal intensity less than the first detected signal intensity;
emitting a first light in the first wavelength and emitting a second light in the second wavelength at the first power level and the second power level, respectively;
detecting the first light and the second light diffused through the epidermis layer and the dermis layer; and
analyzing the detected light;
calculating an oxygen-related energy conversion metabolism and a tissue oxygen requirement from the detected light.

27. The method of claim 26 further comprising the step of determining an index of oxygen delivery for the patient.

28. The method of claim 26 further comprising the step of transmitting data from the physiologic index sensor to a second device.

29. The method of claim 26 further comprising the step of detecting an excess oxygen level at a tissue.

30. A communication system, comprising:
a physiologic index sensor adapted to be in contact with an arm or a chest of a patient wherein the physiologic index sensor further comprises, a first emitter for emitting a first wavelength into an epidermis layer and a dermis layer of the patient wherein the first emitter for emitting the first wavelength is configurable to emit a first target wavelength of from 650 nm to 670 nm, a second emitter for emitting a second wavelength into the epidermis layer and the dermis layer of the patient wherein the second emitter for emitting the second wavelength is configurable to emit a second target wavelength of from 840 nm to 860 nm, a detector optically isolated from the first emitter and the second emitter wherein the detector is configured to detect a first light diffused through the epidermis layer and the dermis layer and a second light diffused through the epidermis layer and the dermis layer, a processor configured to perform an initialization process to determine a first power level of the first emitter having a first detected signal intensity of about 80% of a sensor system A/D converted maximum count limit and a second emitter at the first power level and the second power level, respectively, and receive an input from the detector and calculate an oxygen-related energy conversion metabolism;
a power supply in communication with the physiologic index sensor to power the physiologic index sensor;
a server computer system;
a measurement module on the server computer system for permitting a transmission of a measurement from the physiologic index sensor over a network; and
at least one of an API engine connected to at least one of the physiologic index sensor to create a message about the calculated oxygen-related energy conversion metabolism and transmit the message over an API integrated network to a recipient having a predetermined recipient user name, an SMS engine connected to at least one of a system for detecting physiological parameters and the physiologic index sensor to create an SMS message about the measurement and transmit the SMS message over the network to a recipient device having a predetermined measurement recipient telephone number, or an email engine connected to at least one of the physiologic index sensor to create an email message about the measurement and transmit the email message over the network to a recipient email having a predetermined recipient email address.

31. The communication system of claim 30, further comprising a storing module on the server computer system for storing the measurement in a physiologic index sensor server database.

32. The communication system of claim 31, wherein the physiologic index sensor is connectable to the server computer system over at least one of a mobile phone network or an Internet network, and a browser on a measurement recipient electronic device is used to retrieve an interface on the server computer system.

33. The communication system of claim 32, further comprising: an interface on the server computer system, the interface being retrievable by an application on a mobile device.

34. The communication system of claim 33, wherein the server computer system is connectable over a cellular phone network to receive a response from a measurement recipient mobile device.

35. The communication system of claim 30, further comprising:
a downloadable application residing on a measurement recipient mobile device, the downloadable application transmitting a response and a measurement recipient phone number ID over a cellular phone network to the server computer system, the server computer system utilizing the measurement recipient phone number ID to associate the response with an SMS measurement.

\* \* \* \* \*